United States Patent [19]

Krumkalns

[11] Patent Number: 4,501,746

[45] Date of Patent: Feb. 26, 1985

[54] N,N-DISUBSTITUTED CARBOXAMIDE DERIVATIVES, AND FUNGICIDAL USE THEREOF

[75] Inventor: Eriks V. Krumkalns, Indianapolis, Ind.

[73] Assignee: Eli Lilly and Company, Indianapolis, Ind.

[21] Appl. No.: 418,331

[22] Filed: Sep. 15, 1982

Related U.S. Application Data

[63] Continuation-in-part of Ser. No. 332,022, Dec. 18, 1981, abandoned.

[51] Int. Cl.³ .................... A01N 43/40; C07D 213/56
[52] U.S. Cl. ........................... 514/357; 546/265; 546/270; 546/305; 546/309; 546/331; 546/336; 546/337; 71/93
[58] Field of Search ............... 546/305, 309, 331, 336, 546/337, 265, 270; 424/263

[56] References Cited

U.S. PATENT DOCUMENTS

| | | | |
|---|---|---|---|
| 3,055,906 | 9/1962 | Shapiro et al. | 260/295 |
| 3,128,280 | 7/1964 | Rorig | 260/295 |
| 3,246,975 | 4/1966 | Hopkins et al. | 71/2.5 |
| 3,277,107 | 10/1966 | Neighbors et al. | 260/306.8 |
| 3,277,171 | 10/1966 | Hopkins | 260/557 |
| 3,415,838 | 12/1968 | Crounse et al. | 260/306.8 |
| 3,419,574 | 12/1968 | Hopkins et al. | 260/304 |
| 3,829,307 | 8/1974 | Mihailovski | 71/94 |
| 4,001,256 | 1/1977 | Callahan et al. | 260/295 |
| 4,006,239 | 2/1977 | Mayer et al. | 424/263 |
| 4,358,446 | 11/1982 | Haken et al. | 424/245 |
| 4,359,576 | 11/1982 | Haken et al. | 544/336 |

FOREIGN PATENT DOCUMENTS

| | | |
|---|---|---|
| 1806291 | 5/1970 | Fed. Rep. of Germany . |
| 1465255 | 2/1977 | United Kingdom . |
| 1486459 | 9/1977 | United Kingdom . |
| 1487239 | 9/1977 | United Kingdom . |
| 1490200 | 10/1977 | United Kingdom . |
| 2056974 | 3/1981 | United Kingdom . |
| 196799 | 1/1968 | U.S.S.R. . |

OTHER PUBLICATIONS

Bailey et al., Chem. Abstracts 14181, vol. 77, (1972).
Vinogradova et al., Chem. Abstracts 12410g, vol. 57, (1962).
Walker et al. "Synthesis . . . Amides", J. Med. Chem. 9 624–630, (1966).
Shapiro et al. "N-Dialkylaminoalkyl-N-(pyridylethyl) anilines", J. Pharm. Sci. 50 1035–1037, (1961).
Göber et al. "Stabilitat von Tropicamid", Pharmazie 30 (9), 610–611, (1975).
Derwent Abstract 35319R, Ger. Offen. 1806291, May 14, 1970.
Chemical Abstract 5921f, (1962).
Carelli et al. "Anilidi . . . Locale", Farmaco Ed. Sci. 16, 375–386, (1961).
Chemical Abstract 37–7478g, (1963).
Ponci, et al. "Derivati . . . Antifungina", Farmaco Ed. Sci. 18(4), 288–304, (1963).
Broxton, et al. "The Rates . . . 4-(N'-Alkylacetamido)-pyridines", Aust. J. Chem. 27, 1,053–1,057, (1974).
Abramovitch, et al. "Direct . . . Compounds", J. C. S. Chem. Comm. 956–957, (1979).
Zymalkowski, et al. "Synthesen . . . Kreislaufwirkung", Arch. Pharm. 294, 453–468, (1961).
Chemical Abstract vol. 56 2415e, (1962).
Abramovitch et al. "Direct . . . Rearrangement", J. Het. Chem. 12, 1,079, (1975).
Il'ichev et al. "Derivatives . . . Benzenesulfonamides", Translation from Zhurnal Obshchei Khimii, vol, 43, No. 5, pp. 1,184–1,187, (1973).
Abramovitch et al. "Direct . . . 1-Oxides", J. Org. Chem. vol. 39, No. 13, 1,795–1,802, (1974).
Banitt, et al. "Antiarrhythmics . . . N-(Piperidylalkyl)-trifluroethoxybenzamides", J. Med. Chem. vol. 20, No. 6, 821–826, (1977).
Derwent Abstract 07791D of Belgian Patent 884340, Jan. 16, 1981.
Derwent Abstract H3177, Russian Patent 196799, Jul. 1, 1966.

*Primary Examiner*—Henry R. Jiles
*Assistant Examiner*—Bernard I. Dentz
*Attorney, Agent, or Firm*—Joseph A. Jones; Kathleen R. S. Page; Arthur R. Whale

[57] ABSTRACT

Novel N,N-disubstituted carboxamide derivatives useful as herbicides, fungicides and aquatic plant growth regulators.

29 Claims, No Drawings

N,N-DISUBSTITUTED CARBOXAMIDE DERIVATIVES, AND FUNGICIDAL USE THEREOF

CROSS REFERENCE TO RELATED APPLICATIONS

This is a continuation-in-part of Ser. No. 332,022, filed Dec. 18, 1981 now abandoned.

SUMMARY OF THE INVENTION

The present invention relates to novel N,N-disubstituted carboxamide derivatives that are useful as herbicides, plant growth regulators and plant fungicides. The present invention also provides compositions containing such novel compounds and methods for their use, as well as a novel process to prepare certain of the compounds.

DETAILED DESCRIPTION OF THE INVENTION

The present invention relates to compounds of the formula

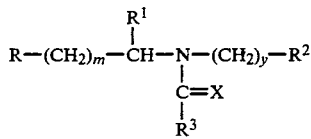

wherein:
R and $R^2$ independently are 3-pyridyl, 4-pyridyl, $C_4-C_{10}$ alkyl, $C_2-C_{10}$ alkenyl, $C_3-C_8$ cycloalkyl, $C_1-C_4$ alkyl substituted $C_3-C_8$ cycloalkyl, 3,4-(methylenedioxy)phenyl or substituted phenyl; provided that at least one of R and $R^2$ is 3-pyridyl or 4-pyridyl;

m and y independently are 0 or 1;
$R^1$ is H or $C_1-C_4$ alkyl;
X is O or S;
$R^3$ is hydrogen, $C_1-C_{10}$ alkyl, $C_1-C_{10}$ haloalkyl, $C_1-C_{10}$ alkoxy, $C_1-C_{10}$ haloalkoxy, $C_3-C_8$ —$C_1-C_4$ alkylene-Z—$R^4$,

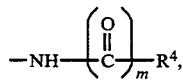

phenyl-$(X)_m$— or substituted phenyl-$(X)_m$—; wherein Z is O, S,

or a direct link;
$R^4$ is $C_1-C_{10}$ alkyl, $C_1-C_{10}$ alkoxy, $C_2-C_{10}$ alkenyl, $C_3-C_8$ cycloalkyl, $C_1-C_4$ haloalkyl, phenyl, or substituted phenyl;
and the agronomically-acceptable salts thereof;
with the proviso that when $R^3$ is —NH-phenyl or —NH-substituted phenyl, $R^2$ is other than a 4 carbon alkyl chain.

In the above formula, $C_1-C_{10}$ alkyl includes methyl, ethyl, n-propyl, isopropyl, n-butyl, sec.-butyl, isobutyl, t-butyl, n-pentyl, isopentyl, sec.-pentyl, neopentyl, n-hexyl, sec.-hexyl, isohexyl, n-heptyl, isoheptyl, sec.-heptyl, n-octyl, sec.-octyl, isooctyl, n-nonyl, sec.-nonyl, isononyl, n-decyl, sec.-decyl, and the like.

$C_2-C_{10}$ Alkenyl includes vinyl, allyl, 1,3-butadienyl, isobutenyl, 2,4-pentadienyl, 2,5-hexadienyl, 1,3,6-heptatrienyl, 3-octenyl, 4,5-nonadienyl, 5-decenyl, and the like.

$C_3-C_8$ Cycloalkyl represents saturated monocyclic cycloalkyl groups such as cyclopropyl, cyclobutyl, cyclopentyl, cyclohexyl, cycloheptyl, and cyclooctyl.

The term "$C_1-C_4$ Alkyl substituted $C_3-C_8$ cycloalkyl" includes 2-methylcyclopropyl, 2,3-dimethylcyclopropyl, 2-isopropylcyclopropyl, 2-t-butylcyclopropyl, 2-ethylcyclobutyl, 1,2-dimethyl-3,4-dipropylcyclobutyl, 2-sec.-butylcyclopentyl, 3,3-dimethylcyclopentyl, 2-ethyl-4-butylcyclohexyl, 3-isobutyl-4,4-diethylcyclohexyl, 2,3,4-trimethyl-5-ethylcycloheptyl, 1-propyl-6-ethylcycloheptyl, 4-n-butylcyclooctyl, 5,6-diethylcyclooctyl, and the like.

$C_1-C_{10}$ Alkoxy includes methoxy, ethoxy, n-propoxy, isopropoxy, n-butoxy, sec.-butoxy, isobutoxy, t-butoxy, n-pentoxy, isopentoxy, sec.-pentoxy, t-pentoxy, n-hexyloxy, sec. hexyloxy, isohexyloxy, t-hexyloxy, and the like.

The terms "halogen" or "halo" represent fluorine, chlorine, bromine and iodine.

$C_1-C_{10}$ Haloalkyl is a $C_1-C_{10}$ alkyl group bearing one or more halo substituents. Such haloalkyl groups include trifluoromethyl, pentabromoethyl, 1-iodo-2,2,2-trifluoroethyl, 3-chloropropyl, 2-iodopropyl, 2-fluoro-2-methylpropyl, 1-iodobutyl, 4-chloropentyl, 3-fluorohexyl, 3-fluorooctyl, 6-chlorodecyl and the like.

$C_1-C_{10}$ Haloalkoxy includes trifluoromethoxy, 1-bromoethoxy, 1,1,2,2-tetrafluoroethoxy, pentafluoroethoxy, 5,5,5-trifluoropentoxy, 4-chlorohexyloxy, and the like.

The term "substituted phenyl" is a phenyl group bearing one or two substituents selected from the group consisting of $C_1-C_6$ alkyl, $C_1-C_6$ alkoxy, halogen, $C_1-C_6$ haloalkyl, $C_1-C_6$ haloalkoxy and nitro. Typical substituted phenyl groups include 2-methyl-5-ethylphenyl, 3-isopropylphenyl, 4-pentafluoroethoxyphenyl, 2,6-dichlorophenyl, 3-methyl-5-pentoxyphenyl, 3-trifluoromethylphenyl, 4,5-dinitrophenyl, 4-methoxyphenyl, and the like.

Agronomically-acceptable salts provided by this invention include both acid addition salts, such as hydrochlorides, hydroiodides, hydrobromides, and the like, and quaternary ammonium salts such as methyl iodides, ethyl iodides, and methyl bromides.

The compounds listed below are typical of the compounds of the present invention. It will be understood that the compounds specifically named herein do not bound the scope of the invention, but are presented merely to assure that agricultural chemists will fully understand this invention.

N-[1-(4-pyridyl)ethyl]-N-(4-fluorophenyl)-α-(n-butylthio)acetamide
N-[(4-pyridyl)methyl]-N-(2,6-difluorophenyl)-α-(n-propylthio)acetamide
N-[1-(3-pyridyl)butyl]-N-(2-nitro-4-trifluoromethylphenyl)-α-(n-methylthio)acetamide
N-[2-(3-pyridyl)propyl]-N-[4-(pentafluoroethoxy)-phenyl]-α-(n-butylthio)acetamide
N-[1-(4-pyridyl)ethyl]-N-(2-(1,1-dimethylethyl)cyclooctyl)-α-(n-propylthio)acetamide
N-[1-(3-pyridyl)propyl]-N-(3,5-dichlorophenyl)decanamide N-[(4-pyridyl)methyl]-N-(2-methyl-3-ethylheptyl)-α-(n-butylthio)acetamide N-[1-(3-pyridyl)ethyl]-N-cyclooctyl-(3,5-difluorophenylamino)carboxamide N-[(4-pyridyl)methyl]-N-(4-fluoro-5-nitrophenyl)-[4-(1-methylpentyl)phenylamino]thiocarboxamide hydrochloride N-[(4-pyridyl)methyl]-N-(4-fluorophenyl)-(t-butylamino)thiocarboxamide N-[(3-pyridyl)methyl]-N-(2,4-dichlorophenyl)heptyloxycarboxamide N-[1-(4-pyridyl)ethyl]-N-(4-ethoxyphenyl)decyloxycarboxamide N-(2,6-diethylphenyl)-N-[(4-pyridyl)methyl]-α-hexylthioacetamide Preferred compounds of the invention have the above formula wherein X is O and R and $R^2$ independently are 3-pyridyl or substituted phenyl with the proviso that at least one of R and $R^2$ is 3-pyridyl.

A particularly preferred group of compounds provided by this invention is defined by the formula

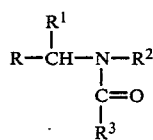

wherein R, $R^1$, $R^2$, and $R^3$ are as defined above. Exemplary of compounds falling within this preferred class are the following:

| R | $R^1$ | $R^2$ | $R^3$ |
|---|---|---|---|
| 3-pyridyl | H | 3-pyridyl | t-butyl |
| 3-pyridyl | H | 4-fluorophenyl | phenyl |
| 4-chlorophenyl | H | 3-pyridyl | H |
| 4-chlorophenyl | H | 3-pyridyl | t-butyl |
| 4-chlorophenyl | H | 3-pyridyl | phenyl |
| 3-pyridyl | H | 4-chlorophenyl | phenyl |
| 3-pyridyl | H | 3-pyridyl | phenyl |
| 3-pyridyl | H | 4-chlorophenyl | t-butyl |
| 4-fluorophenyl | H | 3-pyridyl | t-butyl |
| 3-pyridyl | H | 4-fluorophenyl | t-butyl |
| 4-flurophenyl | H | 3-pyridyl | phenyl |
| 3-pyridyl | H | 3-pyridyl | 4-chlorophenyl |
| 4-fluorophenyl | H | 3-pyridyl | methoxymethyl |
| 3-pyridyl | H | 4-chlorophenyl | methoxymethyl |
| 3-pyridyl | H | 4-chlorophenyl | 4-chlorophenyl |
| 3-pyridyl | H | 4-chlorophenyl | neopentyl |
| 3-pyridyl | H | 4-chlorophenyl | 2-methylphenyl |
| 3-pyridyl | H | 4-chlorophenyl | 2-fluorophenyl |
| 3-pyridyl | H | 4-chlorophenyl | phenoxymethyl |
| 3-pyridyl | H | 4-fluorophenyl | phenoxymethyl |
| 4-chlorophenyl | H | 3-pyridyl | phenoxymethyl |
| 4-chlorophenyl | H | 3-pyridyl | trichloromethyl |
| 4-chlorophenyl | H | 3-pyridyl | 2-fluorophenyl |
| 4-fluorophenyl | H | 3-pyridyl | phenoxymethyl |
| 3-pyridyl | H | phenyl | t-butyl |
| 3-pyridyl | H | 4-bromophenyl | t-butyl |
| 3-pyridyl | $CH_3$ | 4-chlorophenyl | t-butyl |

Another preferred class of compounds provided by the invention have the formula

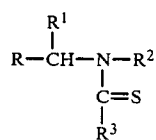

wherein R and $R^2$ independently are 3-pyridyl or substituted phenyl, with the proviso that at least one of R and $R^2$ is 3-pyridyl; $R^1$ is hydrogen or methyl, and $R^3$ is $C_1$–$C_{10}$ alkyl,

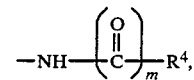

phenyl or substituted phenyl; $R^4$ is $C_1$–$C_{10}$ alkyl, phenyl or substituted phenyl.

The compounds of the present invention may be prepared by methods employing known starting materials that are readily available. A typical procedure of preparing a carboxamide of the invention comprises simply acylating a disubstituted amine. The disubstituted amine that is employed as a starting material can be prepared by reacting an appropriately substituted amine with a carbonyl derivative to form a Schiff base, and then reducing the Schiff base by known procedures, preferably by a palladium on carbon catalyzed hydrogenation reation or by using sodium borohydride in alcohol. The scheme for this reaction is a follows:

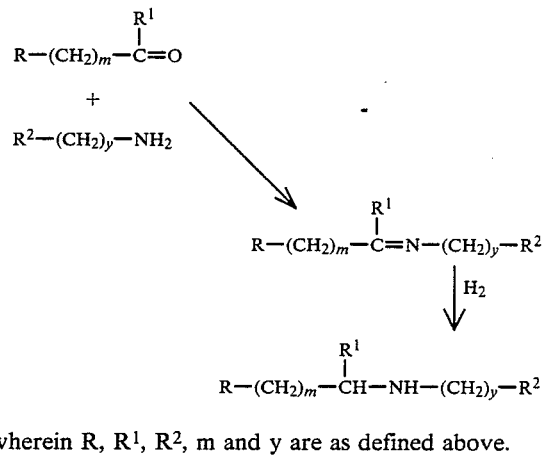

wherein R, $R^1$, $R^2$, m and y are as defined above.

As noted above, a preferred group of compounds comprehended by this invention are carboxamides of the above general formula wherein X is O. These compounds are generally prepared by reacting the disubstituted amine starting material with an acylating agent of the formula

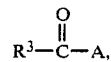

where $R^3$ is defined above and A is a leaving group. Commonly employed acylating agents are acid halides, i.e. where A is halo such as chloro or bromo. Other acylating agents commonly used are acid anhydrides, including mixed anhydrides, for example compounds of the formula

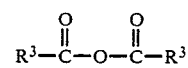

or the like. Carboxylic acids of the above formula wherein A is OH can be employed together with a coupling reagent such as N,N'-dicyclohexylcarbodiimide to effect acylation of the disubstitued amine starting materials.

The reaction of a disubstituted amine with an acid halide to provide a compound of this invention is depicted by the following scheme:

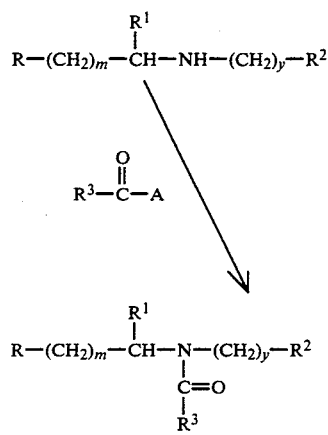

wherein R, $R^1$, $R^2$, $R^3$, m and y are as defined, and A is halo. This procedure is well known to those skilled in the art and may be performed in a variety of ways. Typically, the reaction is carried out in the presence of an excess of a base such as triethylamine to act as an acid scavenger. The reaction can be performed in any number of acceptable organic solvents, for example dioxane, diglyme, benzene, toluene or the xylenes. The reaction is preferably run at a temperature of about 25° C., but will generally take place at a temperature in the range of from about −50° C. to 200° C. Typically, following addition of the acid halide to the reaction mixture, the product either precipitates out of solution or can be isolated following removal of the solvent under reduced pressure. The compound of the present invention may then be further purified if desired by recrystallization or column chromatography according to known procedures.

The reaction of an anhydride with a disubstituted amine to provide a compound of this invention is depicted by the following scheme:

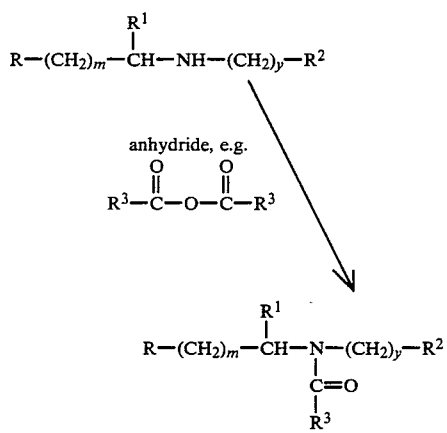

This reaction is generally performed by reacting approximately equimolar quantities of disubstituted amine and anhydride in a suitable solvent and at a temperature of about 20° C. to 150° C., preferably at the reflux temperature of the reaction mixture. Suitable solvents include most aprotic organic solvents, with carbon tetrachloride, 1,2-dichloroethane, the xylenes, toluene and benzene being preferred. The anhydride may, if desired, be employed in excessive amounts so as to serve as the reaction solvent as well as a reactant. The reaction time ranges from about 10 minutes to about 3 days in length. The reaction is then worked up according to standard procedures. Typically, the reaction solvent is removed by evaporation, for example under reduced pressure, and the product is then purified by crystallization or column chromatography, or any other procedure well known to people skilled in the art of organic chemistry.

Carboxylic acids react with disubstituted amines in the presence of a coupling reagent to provide compounds of this invention according to the following scheme:

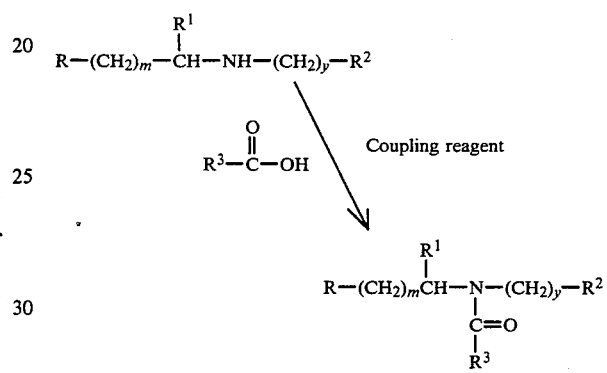

This reaction is generally performed in a suitable solvent and at a moderate temperature. Suitable solvents include most halogenated hydrocarbons such as methylene chloride, chloroform and 1,2-dichloroethane. Methylene chloride is the solvent of choice. The reaction may be performed at a temperature ranging from 0° to 100° C., preferably at about 25° C. The reaction time typically ranges from about 1 to about 48 hours. It should be noted that longer or shorter reaction times may be employed depending on the concentration of reactants, temperature, and the like. It is also preferred to have a slight excess of the carboxylic acid in the reaction mixture, for instance about 0.1 to about 1 molar excess. Coupling reagents commonly employed are any of those used in the peptide art for formation of peptide bonds. Such agents include DDC (dicyclohexylcarbodiimide), diisopropylcarbodiimide, EEDQ (N-ethoxycarbonyl-2-ethoxy-1,2-dihydroquinoline), and the like. Upon completion of the reaction, the reaction mixture is worked up according to standard procedures. Typically, the reaction mixture is filtered, and the filtrate is concentrated in vacuo. The resulting residue may then be purified by procedures well known in the art, for example by crystallization, distillation or column chromatography.

Any of the above described acylation reactions can be employed to synthesize compounds of the invention where $R^3$ in the above general formula is other than

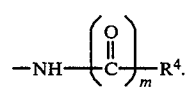

Compounds wherein $R^3$ is —$C_1$-$C_4$ alkylene —Z—$R^4$ in which Z is S can be prepared by an alternative process that is provided as a further embodiment of the invention. Such process comprises reacting a substituted thiazolidinone with a strong alkali metal base of the formula $R^4$—M, where M is an alkali metal such as lithium or sodium. The reaction can, if desired, be carried out in the presence of a $C_1$-$C_4$ alkyl halide so as to provide compounds of the invention wherein $R^1$ is $C_1$-$C_4$ alkyl. The overall reaction scheme is depicted as follows:

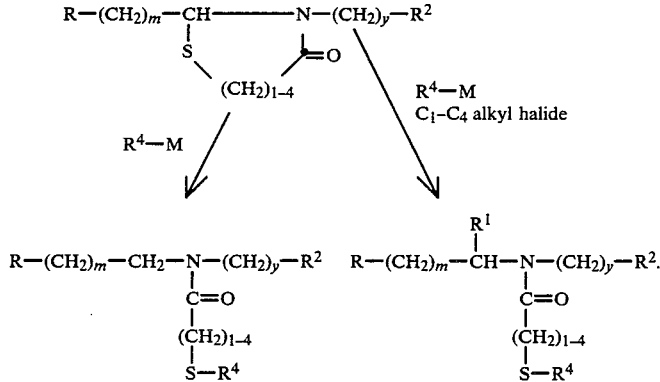

This reaction is generally performed by adding the thiazolidinone and at least a twofold excess of an alkali metal derivative $R^4$—M in a mutual solvent. The thiazolidinone that is employed is disclosed in European Patent No. 4129. The reaction is carried out in an organic solvent and preferably in an inert atmosphere such as nitrogen or argon. Suitable solvents should be substantially water-free (i.e. less than about 1% water v/v) and include most aprotic solvents. The solvents of choice are the ethers, preferably tetrahydrofuran, diglyme, dioxane and diethyl ether. The temperature range suitable for addition of the reactants can be from about −100° C. to about 0° C., −80° C. to −30° C. being preferred. Following addition of the reactants, the temperature of the reaction mixture is maintained in the range of from about −100° C. to 25° C., preferably −80° to 0° C. Following formation of the product, which usually occurs after about 30 minutes to 10 hours, the mixture is allowed to warm to room temperature and is worked up according to standard procedures. Typically water is added to the reaction mixture and the organic phase is separated. Following removal of the solvent under reduced pressure, the product may be purified by either crystallization or chromatography according to procedures well known in the art.

A procedure which can be employed to prepare the compounds of the present invention wherein $R^3$ is

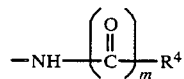

comprises reacting a disubstituted amine starting material with a substituted isocyanate or iso(thio)cyanate as follows:

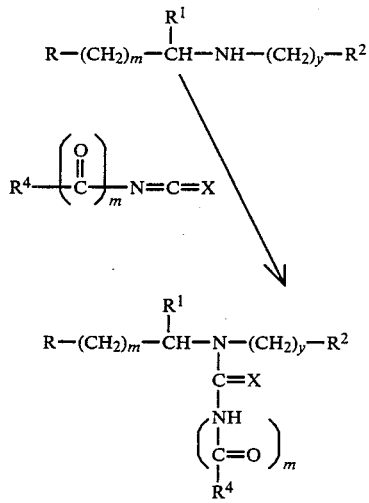

wherein R, $R^1$, $R^2$, $R^4$, m and y are as defined above.

This reaction is generally carried out by combining approximately equimolar quantities of the amine and isocyanate analog in an aprotic solvent and at a temperature in the range of from about 10° C. to about 150° C. The preferred temperature range is from about 25° C. to the reflux temperature of the reaction mixture. Suitable aprotic solvents include ethyl acetate, chloroform, benzene and the like. Ethyl acetate is the solvent of choice. The product is usually formed after about one hour to about 2 days depending on the specific reactants involved. The reaction is then worked up according to procedures well known in the art. Typically, either the precipitated solid is collected or the solvent is removed in vacuo. The product can then be purified by standard procedures such as crystallization or column chromatography.

As noted hereinabove, a preferred group of compounds provided by the invention have the above general formula wherein X is O. Such compounds are useful not only as herbicides, plant growth regulators and fungicides, but also can serve as intermediates in the preparation of compounds wherein X is S. For example, reaction of an N,N-disubstituted carboxamide (X=O) with a thiating agent provides the corresponding N,N-disubstituted thiocarboxamide (X=S). Typical thiating agents include phosphorus pentasulfide, and more preferably Lawesson's Reagent, which is 2,4-bis(4-methoxyphenyl)-1,3-dithia-2,4-diphosphetane-2,4-disulfide.

This thiating agent and its use are described in detail in *Tetrahedron Letters,* 21, 4061 (1980).

The thiation reaction generally is accomplished by combining approximately equimolar quantities of carboxamide and thiating agent in a mutual organic solvent such as toluene or dioxane. The reaction is generally complete within about 2 to 10 hours when carried out at a temperature of about 50° C. to about 150° C. The thiocarboxamide derivative (wherein X=S) is isolated and purified by standard methods.

Because all of the compounds comprehended by this invention have at least one pyridyl moiety as part of the chemical structure, the compounds are basic in nature and readily form salts at the pyridine nitrogen atom. Salts are typically formed by reacting a carboxamide derivative of the above general formula with an equimolar or excess amount of acid or lower alkyl alkylating agent. The reactants are generally combined in a mutual solvent such as diethyl ether or benzene, and the salt normally precipitates out of solution within one hour to about 10 days, and can be isolated by filtration.

The following detailed Examples are provided in an effort to more fully illustrate specific aspects of this invention. In addition to the given physical chemistry data, each compound structure was verified by nuclear magnetic resonance (NMR). Infrared spectroscopy (IR) was performed for certain of these compounds as well. The examples are not intended to be limiting in any respect and should not be so construed. Example 1 illustrates the novel reaction of a thiazolidinone with an alkylating agent to provide a compound of this invention.

EXAMPLE 1

N-[1-(3-pyridyl)ethyl]-N-(4-fluorophenyl)-α-(n-butylthio)acetamide (A) Preparation of 3-(4-fluorophenyl)-2-(3-pyridyl)-4-thiazolidinone To a stirred solution of 55.5 g. of 4-fluoroaniline in 500 ml. of toluene were added in one portion 53.5 g. of 3-pyridylcarboxaldehyde and 46.0 g. of thioglycolic acid. The reaction mixture was heated at reflux for four hours and water was removed via a Dean-Stark trap. The reaction mixture was then cooled and concentrated by evaporation of the solvent under reduced pressure. The solid which remained was crystallized from diethyl ether and acetone to give 70.0 g. of 3-(4-fluorophenyl)-2-(3-pyridyl)-4-thiazolidinone. M.P. 161° C.

(B) A solution comprised of 71 ml. of n-butyl lithium in 500 ml. of tetrahydrofuran was stirred and cooled to −70° C. in a dry ice/acetone bath. To the cold stirred reaction mixture was added dropwise over one hour a solution of 13.7 g. of 3-(4-fluorophenyl)-2-(3-pyridyl)-4-thiazolidinone in 100 ml. of tetrahydrofuran. After the addition was completed, the reaction mixture was stirred at −70° C. for about thirty minutes, and then 22 g. of methyl iodide were added in one portion. The reaction mixture was then stirred at −70° C. for four hours, and finally for one hour at room temperature. The reaction mixture was next diluted by the addition of 200 ml. of water. The organic layer was separated, dried, and the solvent was removed by evaporation under reduced pressure to provide the product as an oil. The oil was purified by chromatography over silica gel, eluting with toluene and acetone. Fractions containing the major component were combined and the solvent was evaporated therefrom to afford 1.4 g. of N-[1-(3-pyridyl)ethyl]-N-(4-fluorophenyl)-α-(n-butylthio)acetamide as an oil.

Analysis calculated for $C_{19}H_{23}FN_2OS$: Theory: C,65.90; H,6.65; N,8.09; Found: C,66.04; H,6.99; N,7.92.

EXAMPLE 2

N-[(3-pyridyl)methyl]-N-(4-chlorophenyl)-α-(n-butylthio)acetamide (A) Preparation of N-(4-chlorophenyl)-[(3-pyridyl)methyl]amine A solution of 127.6 g. (1.0 mole) of 4-chloroaniline in 500 ml. of toluene containing 99 ml. (1.05 mole) of 3-pyridinecarboxaldehyde and 300 mg. of para-toluenesulfonic acid was heated at reflux for eight hours. The water which formed during the reaction was collected and removed via a Dean-Stark trap. The reaction mixture was cooled to room temperature and the solvent was removed by evaporation under reduced pressure to provide a solid product. The solid was crystallized from diethyl ether to give 119.2 g. of N-(4-chlorophenyl)-[(3-pyridyl)methyl]imine. M.P. 61°–65° C.

A solution of 88.0 g. of the compound thus prepared in 200 ml. of ethanol containing 20.0 g. of sodium borohydride was stirred at ambient temperature for sixteen hours. Evaporation of the solvent under reduced pressure afforded a solid that was washed with water and triturated with petroleum ether and with diethyl ether to give 27.5 g. of N-(4-chlorophenyl)-[(3-pyridyl)methyl]amine. M.P. 95°–96° C.

(B) To a stirred solution of 3.4 g. of α-(n-butylthio)acetic acid in 200 ml. of dichloromethane containing 5.0 g. of N-(4-chlorophenyl)-[(3-pyridyl)methyl]amine were added portionwise 4.7 g. of N,N'-dicyclohexylcarbodiimide. The reaction mixture was stirred at room temperature for forty-eight hours. The precipitated N,N'-dicyclohexylurea was removed by filtration, and the filtrate was concentrated to dryness by evaporation of the solvent under reduced pressure. The product thus formed was purified by chromatography over silica gel, eluting with 10% v/v acetone/toluene. The appropriate fractions were combined and the solvent was removed by evaporation under reduced pressure to provide 2.3 g. of N-[(3-pyridyl)methyl]-N-(4-chlorophenyl)-α-(n-butylthio)acetamide. Oil Analysis calculated for $C_{18}H_{21}ClN_2OS$: Theory: C,61.97; H,6.07; N,8.03; Found: C,61.92; H,6.12; N,7.82.

EXAMPLE 3

N-[(3-pyridyl)methyl]-N-(4-fluorophenyl)-α-(n-butylthio)acetamide was prepared by the method of Example 2 by reacting 10.1 g. of N-(4-fluorophenyl)-[(3-pyridyl)methyl]amine with 7.4 g. of α-(n-butylthio)acetic acid and 10.3 g. of N,N'-dicyclohexylcarbodiimide in 250 ml. of dichloromethane. Weight 6.5 g. as an oil.

Analysis calculated for $C_{18}H_{21}FN_2OS$: Theory: C,65.03; H,6.37; N,8.43; Found: C,63.79; H,6.11; N,8.37.

EXAMPLE 4

N-[(3-pyridyl)methyl]-N-cyclohexyl-α-(n-butylthio)acetamide was prepared by the method of Example 2 by reacting 9.5 g. of N-cyclohexyl-[(3-pyridyl)methyl]amine with 7.4 g. of α-(n-butylthio)acetic acid and 9.0 g. of N,N'-dicyclohexylcarbodiimide in 150 ml of toluene. Weight 3.5 g. as an oil.

Analysis calculated for $C_{18}H_{28}N_2OS$: Theory: C,67.46; H,8.81; N,8.74; Found: C,67.21; H,8.59; N,8.53.

EXAMPLE 5

N-[1-(3-pyridyl)ethyl]-N-cyclohexyl-α-(n-butylthio)acetamide was prepared by the method of Example 2 by reacting 5.0 g. of N-cyclohexyl-[1-(3-pyridyl)ethyl]amine with 3.6 g. of α-(n-butylthio)acetic acid and 5.0 g. of N,N'-dicyclohexylcarbodiimide in 200 ml. of dichloromethane. Oil.

Analysis calculated for $C_{19}H_{30}N_2OS$: Theory: C,68.22; H,9.05; N,8.37; Found: C,67.99; H,8.95; N,8.27.

EXAMPLE 6

N-[(3-pyridyl)methyl]-N-(4-chlorophenyl)-3-(n-butylthio)propanamide was prepared by the general procedure of Example 2 by reacting 5.0 g. of N-(4-chlorophenyl)-[(3-pyridyl)methyl]amine with 3.6 g. of α-(n-butylthio)propionic acid and 4.7 g. of N,N'-dicyclohexylcarbodiimide in 200 ml. of dichloromethane. Oil.

Analysis calculated for $C_{19}H_{23}ClN_2OS$: Theory: C,62.88; H,6.39; N,7.72; Found: C,62.67; H,6.39; N,7.98.

EXAMPLE 7

N-(3-pyridyl)-N-[(4-chlorophenyl)methyl]-α-(n-butylthio)acetamide was prepared by reacting 5.0 g. of N-(3-pyridyl)-[(4-chlorophenyl)methyl]amine with 3.5 g. of α-(n-butylthio)acetic acid and 5.0 g. of N,N'-dicyclohexylcarbodiimide in 100 ml. of dichloromethane according to the method of Example 2. Weight collected was 3.9 g as an oil.

Analysis calculated for $C_{18}H_{21}ClN_2OS$: Theory: C,60.61; H,6.28; N,8.32; Found: C,60.85; H,6.02; N,8.04.

EXAMPLE 8

N-[2-(4-pyridyl)ethyl]-N-cyclohexyl-α-(n-butylthio)acetamide was prepared by reacting 5.0 g. of N-cyclohexyl-[2-(4-pyridyl)ethyl]amine with 4.4 g. of α-(n-butylthio)acetic acid and 5.0 g. of N,N'-dicyclohexylcarbodiimide in 100 ml. of dichloromethane by the method of Example 2. Weight 2.57 g. Oil.

Analysis calculated for $C_{19}H_{30}N_2OS$: Theory: C,68.26; H,8.98; N,8.38; Found: C,66.05; H,8.95; N,8.30.

EXAMPLE 9

N-[(3-pyridyl)methyl]-N-(1,1-dimethylethyl)-α-(n-butylthio)acetamide was prepared by the method of Example 2 by reacting 8.2 g. of N-[(3-pyridyl)methyl]-(1,1-dimethylethyl)amine with 7.4 g. of α-(n-butylthio)acetic acid and 10.3 g. of N,N'-dicyclohexylcarbodiimide in 150 ml. of dichloromethane. Weight 1.6 g. M.P. 55°–56° C.

Analysis calculated for $C_{16}H_{26}N_2OS$: Theory: C,65.26; H,8.90; N,9.51; Found: C,65.07; H,8.67; N,9.32.

EXAMPLE 10

N-(1-methylhexyl)-N-[(3-pyridyl)methyl]-α-(n-butylthio)acetamide was prepared by the method of Example 2 by reacting 3.6 g. of α-(n-butylthio)acetic acid and 5.0 g. of N,N'-dicyclohexylcarbodiimide with 5.0 g. of N-(1-methylhexyl)-[(3-pyridyl)methyl]amine in 200 ml. of dichloromethane. Oil.

Analysis calculated for $C_{19}H_{32}N_2OS$: Theory: C,67.81; H,9.58; N,8.32; Found: C,66.54; H,9.80 N,8.21.

EXAMPLE 11

N-[1-(3-pyridyl)ethyl]-N-(4-chlorophenyl)hexanamide

To a stirred solution of 7.5 g. of N-(4-chlorophenyl)-[1-(3-pyridyl)ethyl]amine in 200 ml. of toluene containing 5.0 g. of triethylamine were added dropwise over thirty minutes 4.5 g. of hexanoyl chloride. Following the complete addition, the solid precipitate which had formed was removed by filtration, and the solvent was removed from the filtrate by evaporation under reduced pressure. The product thus formed was chromatographed over a silica gel column to provide, after removal of the solvent from the appropriate factions, 650 mg. of N-[1-(3-pyridyl)ethyl]-N-(4-chlorophenyl)hexanamide. Oil.

Analysis calculated for $C_{19}H_{23}ClN_2O$: Theory: C,68.97; H,7.01; N,8.47; Found: C,69.03; H,7.06; N,8.22.

EXAMPLE 12

N-[(3-pyridyl)methyl]-N-(4-chlorophenyl)acetamide was prepared by reacting 5.0 g. of N-(4-chlorophenyl)-[(3-pyridyl)methyl]amine with 2.0 g. of acetyl chloride in 250 ml. containing 3.0 g. of triethylamine according to the method of Example 11. Weight 1.1 g. M.P. 64°–65° C.

Analysis calculated for $C_{14}H_{13}ClN_2O$: Theory: C,64.50; H,5.03; N,10.74; Found: C,64.28; H,4.92; N,10.47.

EXAMPLE 13

The procedure of Example 11 was followed to react 3.0 g. of N-(4-chlorophenyl)-[(3-pyridyl)methyl]amine with 1.84 g. of hexanoyl chloride and 2.0 g. of triethylamine in 50 ml. of toluene to afford 0.9 g. of N-[(3-pyridyl)methyl]-N-(4-chlorophenyl)hexanamide, as an oil.

Analysis calculated for $C_{18}H_{21}ClN_2O$: Theory: C,68.25; H,6.64; N,8.85; Found: C,67.86; H,6.55; N,8.35.

EXAMPLE 14

N-[(3-pyridyl)methyl]-N-(4-fluoropheny)heptanamide

A solution of 5.0 g. of N-(4-fluorophenyl)-[(3-pyridyl)methyl]amine and 3.2 g. of n-heptanoic acid in 100 ml. of dichloromethane containing 5.0 g. of N,N'-dicyclohexylcarbodiimide was stirred at room temperature for fifty-six hours. The precipitated solids were removed by filtration, and the solvent was removed from the filtrate by evaporation under reduced pressure to provide an oil. The oil was purified by chromatography over a silica gel column, eluting with ethyl acetate. The appropriate fractions were collected, combined, and the solvent was removed by evaporation to provide 600 mg. of an oil identified as N-[(3-pyridyl)methyl]-N-(4-fluorophenyl)heptanamide.

Analysis calculated for $C_{19}H_{23}FN_2O$: Theory: C,72.58; H,7.37; N,8.91; Found: C,72.34; H,7.37; N,8.70.

EXAMPLES 15–18

The following carboxamides were prepared by reacting N-(4-fluorophenyl)-[(3-pyridyl)methyl]amine with the appropriate carboxylic acid and N,N'-dicyclohexylcarbodiimide in dichloromethane according to the general procedure of Example 14.

N-[(3-pyridyl)methyl]-N-(4-fluorophenyl)-α-(4-chlorophenoxy)acetamide. M.P. 69°–70° C. Weight 10.0 g.

Analysis calculated for $C_{20}H_{16}ClFN_2O_2$: Theory: C,64.78; H,4.35; N,7.55; Found: C,64.60; H,4.54; N,7.38.

N-[(3-pyridyl)methyl]-N-(4-fluorophenyl)-[3-(4-bromobenzoyl)]propanamide. Oil.

Analysis calculated for $C_{22}H_{18}BrFN_2O_2$: Theory: C,59.88; H,4.11; N,6.35; Found: C,59.93; H,4.02; N,6.37.

N-[(3-pyridyl)methyl]-N-(4-fluorophenyl)-α-cyclohexylacetamide. Oil.

N-[(3-pyridyl)methyl]-N-(4-fluorophenyl)cyclopentylcarboxamide. Oil.

EXAMPLE 19

N-[(3-pyridyl)methyl]-N-(4-fluorophenyl)-α,α,α-trifluoroacetamide

A solution made up of 4.0 g. of N-(4-fluorophenyl)-[(3-pyridyl)methyl]amine and 15 ml. of trifluoroacetic anhydride in 100 ml. of carbon tetrachloride was heated at reflux for one hour. The reaction mixture was cooled and the solvent was removed by evaporation under reduced pressure to provide a solid. The solid was crystallized from diethyl ether to afford 6.0 g. of N-[(3-pyridyl)methyl]-N-(4-fluorophenyl)-α,α,α-trifluoroacetamide. M.P. 97°–98° C.

EXAMPLE 20

N-[(3-pyridyl)methyl]-N-(4-chlorophenyl)-α,α,α-trifluoroacetamide was prepared by the method of Example 19 by reacting 4.5 g. of N-(4-chlorophenyl)-[(3-pyridyl)methyl]amine with 10 ml. of trifluoroacetic anhydride in 50 ml. of 1,2-dichloroethane. Weight 3 g. M.P. 80°–81° C.

EXAMPLE 21

N-[(3-pyridyl)methyl]-N-(4-fluorophenyl)-(3-chlorophenylamino)carboxamide

A solution of 5.0 g. of N-(4-fluorophenyl)-[(3-pyridyl)methyl]amine and 3.76 g. of 3-chlorophenylisocyanate in 200 ml. of ethyl acetate was stirred at room temperature for sixteen hours. The product had precipitated and was collected by filtration and air dried to provide 8.0 g. of N-[(3-pyridyl)methyl]-N-(4-fluorophenyl)-(3-chlorophenylamino)carboxamide. M.P. 189°–190° C.

Analysis calculated for $C_{19}H_{15}ClFN_3O$: Theory: C,64.14; H,4.25; N,11.81; Found: C,64.17; H,4.24; N,12.09.

EXAMPLE 22

Four grams of 2-chlorobenzoylisoxyanate were reacted with 4.0 g. of N-(4-fluorophenyl)-[(3-pyridyl)methyl]amine in 100 ml. of ethyl acetate by the method of Example 21 to give 7.0 g. of N-[(3-pyridyl)methyl]-N-(4-fluorophenyl)-(2-chlorobenzoylamino)carboxamide. M.P. 158° C.

EXAMPLE 23

N-[(3-pyridyl)methyl]-N-(4-fluorophenyl)-(4-chlorophenylamino)carboxamide was prepared by the method of Example 21 by reacting 5.0 g. of N-(4-fluorophenyl)-[(3-pyridyl)methyl]amine with 3.76 g. of 4-chlorophenylisocyanate in 200 ml. of ethyl acetate. Weight 1.8 g. M.P. 95°–96° C.

Analysis calculated for $C_{19}H_{15}ClFN_3O$: Theory: C,64.14; H,4.25; N,11.81; Found: C,64.10; H,4.54; N,11.78.

EXAMPLE 24

By following the procedure of Example 21, 6.4 g. of N-(2-chlorophenyl)-[(3-pyridyl)methyl]amine were reacted with 4.0 g. of 2-chlorobenzoylisocyanate in 100 ml. of ethyl acetate to provide, following crystallization from ethyl acetate, 3.0 g. of N-[(3-pyridyl)methyl]-N-(2-chlorophenyl)-(2-chlorobenzoylamino)carboxamide. M.P. 119°–120° C.

EXAMPLE 25

N-[(3-pyridyl)methyl]-N-(4-fluorophenyl)-(4-nitrophenylamino)thiocarboxamide

A solution of 5.0 g. of N-(4-fluorophenyl)-[(3-pyridyl)methyl]amine and 4.5 g. of 4-nitrophenylisothiocyanate in 250 ml. of ethyl acetate was heated at reflux for eight hours. The reaction mixture was cooled to room temperature and the precipitated solid was collected by filtration and air dried to give 8.0 g. of N-[(3-pyridyl)methyl]-N-(4-fluorophenyl)-(4-nitrophenylamino)thiocarboxamide. M.P. 132°–133°.

Analysis calculated for $C_{19}H_{15}FN_4O_2S$: Theory: C,59.68; H,3.93; N,14.66; Found: C,59.69; H,4.07; N,14.70.

EXAMPLE 26–28

By following the general procedure of Example 25, the following thiocarboxamides were prepared.

N-[(3-pyridyl)methyl]-N-(4-fluorophenyl)-(n-heptylamino)thiocarboxamide. 1.2 g. of oil.

Analysis calculated for $C_{20}H_{26}FN_3S$: Theory: C,66.82; H,7.29; N,11.69; Found: C,66.59; H,7.13; N.11.40.

N-[(3-pyridyl)methyl]-N-(4-fluorophenyl)-(3-chlorophenylamino)thiocarboxamide. M.P. 117°–118° C.

Analysis calculated for $C_{19}H_{15}ClFN_3S$: Theory: C,61.37; H,4.07; N,11.30; Found: C,61.29; H,4.32; N,11.09.

N-[(3-pyridyl)methyl]-N-(4-fluorophenyl)-(cyclohexylamino)thiocarboxamide. M.P. 132°–133° C.

Analysis calculated for $C_{19}H_{22}FN_3S$: Theory: C,66.44; H,6.46; N,12.23; Found: C,66.17; H,6.28; N,12.19.

The following examples further illustrate the synthesis of preferred compounds of the invention defined by the formula

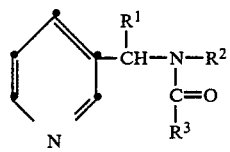

| Example No. | R¹ | R² | R₃ | M.P. | | C | H | N |
|---|---|---|---|---|---|---|---|---|
| 29 | H | 2,6-dimethylphenyl | 1-ethyl-1-methylpropyl | Oil | Theory: | 75.89 | 8.50 | 8.28 |
| | | | | | Found: | 75.95 | 8.47 | 8.20 |
| 30 | H | 1-methylhexyl | 4-methoxyphenyl | Oil | Theory: | 74.08 | 8.29 | 8.23 |
| | | | | | Found: | 73.87 | 8.12 | 8.09 |
| 31 | H | 4-chlorophenyl | 1,1-dimethylethyl | 78°–80° C. | Theory: | 67.43 | 6.32 | 9.25 |
| | | | | | Found: | 67.26 | 6.15 | 9.16 |
| 32 | H | 4-chlorophenyl | phenoxy | Oil | Theory: | 67.36 | 4.46 | 8.27 |

-continued

| Example No. | R¹ | R² | R₃ | M.P. | | C | H | N |
|---|---|---|---|---|---|---|---|---|
| 33 | H | 2,6-difluorophenyl | cyclopropyl | Oil | Found: | 67.12 | 4.37 | 8.49 |
| | | | | | Theory: | 66.66 | 4.89 | 9.72 |
| | | | | | Found: | 66.42 | 4.82 | 9.96 |
| 34 | H | 4-chlorophenyl | 2-chlorophenyl | Oil | Theory: | 63.88 | 3.95 | 7.84 |
| | | | | | Found: | 64.01 | 3.74 | 7.90 |
| 35 | H | 4-chlorophenyl | 4-chlorophenoxymethyl | Oil | Theory: | 62.03 | 4.16 | 7.23 |
| | | | | | Found: | 58.79 | 3.81 | 6.52 |
| 36 | H | 4-chlorophenyl | cyclopropyl | 80°–83° C. | Theory: | 67.02 | 5.27 | 9.77 |
| | | | | | Found: | 66.81 | 5.10 | 9.55 |
| 37 | H | 4-chlorophenyl | methoxy | Oil | Theory: | 60.77 | 4.74 | 10.12 |
| | | | | | Found: | 60.54 | 4.69 | 9.83 |
| 38 | H | 4-chlorophenyl | methoxymethyl | Oil | Theory: | 62.70 | 5.26 | 9.75 |
| | | | | | Found: | 61.55 | 4.93 | 9.32 |
| 39 | H | 2,6-difluorophenyl | chloromethyl | 102°–103° C. | Theory: | 65.45 | 4.58 | 12.72 |
| | | | | | Found: | 65.23 | 4.76 | 12.60 |
| 40 | H | cyclohexyl | 4-methoxyphenyl | Oil | Theory: | 74.05 | 7.46 | 8.63 |
| | | | | | Found: | 73.98 | 7.25 | 8.43 |
| 41 | CH₃ | 4-fluorophenyl | cyclopropyl | Oil | Theory: | 71.81 | 6.03 | 9.85 |
| | | | | | Found: | 72.02 | 5.83 | 9.69 |
| 42 | CH₃ | 4-fluorophenyl | 2-cyclohexylethyl | Oil | Theory | 74.09 | 7.40 | 8.23 |
| | | | | | Found: | 73.88 | 7.17 | 8.50 |
| 43 | H | cyclohexyl | 1,1-dimethylethyl | Oil | Theory: | 74.41 | 9.55 | 10.21 |
| | | | | | Found: | 73.69 | 7.96 | 9.54 |
| 44 | H | 2,4-dichlorophenyl | 1,1-dimethylethyl | Oil | Theory: | 60.54 | 5.38 | 8.31 |
| | | | | | Found: | 57.69 | 5.32 | 7.63 |
| 45 | H | 2,6-diethylphenyl | n-propyl | Oil | | | | |
| 46 | H | 2,6-diethylphenyl | methyl | Oil | Theory: | 65.54 | 7.85 | 9.92 |
| | | | | | Found: | 64.81 | 7.49 | 9.36 |
| 47 | CH₃ | 2,6-dimethylphenyl | n-propyl | Oil | Theory: | 76.99 | 8.16 | 9.45 |
| | | | | | Found: | 76.79 | 7.97 | 9.40 |
| 48 | CH₃ | 2,6-dimethylphenyl | methyl | Oil | Theory: | 76.09 | 7.51 | 10.44 |
| | | | | | Found: | 75.84 | 7.41 | 10.16 |
| 49 | CH₃ | 3,5-dimethylphenyl | n-propyl | Oil | Theory: | 79.21 | 7.60 | 13.20 |
| | | | | | Found: | 78.98 | 7.72 | 13.02 |
| 50 | H | 2,6-dimethylphenyl | 1,1-dimethylethyl | 80°–82° C. | Theory: | 76.99 | 8.16 | 9.45 |
| | | | | | Found: | 76.41 | 7.23 | 10.35 |
| 51 | H | 2,6-dimethylphenyl | n-propyl | Oil | | | | |
| 52 | H | 2,6-difluorophenyl | 1,1-dimethylethyl | Oil | Theory: | 67.09 | 5.96 | 9.20 |
| | | | | | Found: | 66.82 | 5.81 | 8.97 |
| 53 | H | 2,6-dimethylphenyl | trifluoromethyl | Oil | | | | |
| 54 | H | 2,6-dimethylphenyl | methyl | Oil | | | | |
| 55 | H | 2-chlorophenyl | 1,1-dimethylethyl | Oil | Theory: | 67.43 | 6.32 | 9.25 |
| | | | | | Found: | 59.78 | 5.82 | 7.75 |
| 56 | CH₃ | 4-chlorophenyl | 1,1-dimethylphenyl | Oil | Theory: | 68.24 | 6.68 | 8.84 |
| | | | | | Found: | 68.03 | 6.83 | 9.01 |
| 57 | H | 2-methyl-4-chloro-phenyl | 1,1-dimethylethyl | Oil | Theory: | 68.25 | 6.64 | 8.85 |
| | | | | | Found: | 67.53 | 6.49 | 8.74 |
| 58 | H | 2,6-dimethylphenyl | ethylamino | 68°–70° C. | Theory: | 73.28 | 8.09 | 13.49 |
| | | | | | Found: | 73.28 | 7.90 | 13.38 |
| 59 | H | 2-ethyl-6(1-methylpropyl)phenyl | 2-chloroethylamino | Oil | Theory: | 67.45 | 7.55 | 11.24 |
| | | | | | Found: | 65.58 | 7.16 | 10.70 |
| 60 | H | 4-fluorophenyl | 2-cyclopentylethyl | Oil | | | | |
| 61 | H | 2,6-diethylphenyl | n-heptyl | Oil | Theory: | 78.64 | 9.34 | 7.64 |
| | | | | | Found: | 78.42 | 9.22 | 7.41 |
| 62 | H | 2,6-diethylphenyl | n-butylthiomethyl | Oil | Theory: | 71.31 | 8.16 | 7.56 |
| | | | | | Found: | 71.32 | 8.16 | 7.56 |
| 63 | H | 1,1-dimethylethyl | 4-chlorophenoxymethyl | Oil | Theory: | 64.96 | 6.36 | 8.42 |
| | | | | | Found: | 65.01 | 6.34 | 8.31 |
| 64 | H | 2-chlorophenyl | ethylcarbonylmethoxy | Oil | Theory: | 61.36 | 5.15 | 8.42 |
| | | | | | Found: | 61.16 | 4.98 | 8.21 |
| 65 | CH₃ | 2,6-dimethylphenyl | ethylamino | Oil | Theory: | 72.70 | 7.80 | 14.13 |
| | | | | | Found: | 73.88 | 7.00 | 12.60 |
| 66 | H | 4-chlorophenyl | 2-chloroethylamino | 75°–78° C. | Theory: | 59.46 | 4.99 | 8.67 |
| | | | | | Found: | 59.24 | 4.75 | 8.62 |
| 67 | H | 2,6-dimethylphenyl | chloromethyl | 125°–126° C. | Theory: | 79.21 | 7.60 | 13.20 |
| | | | | | Found: | 78.96 | 7.50 | 12.90 |
| 68 | H | 4-chlorophenyl | 2-chloroethylamino | Oil | Theory: | 55.57 | 4.66 | 12.96 |
| | | | | | Found: | 55.30 | 4.72 | 12.76 |
| 69 | H | 2,6-dimethylphenyl | 2-chloroethylamino | Oil | Theory: | 64.25 | 6.34 | 13.22 |
| | | | | | Found: | 64.02 | 6.17 | 13.03 |

The present invention also encompasses the agronomically-acceptable salts of the carboxamides of the invention. The synthesis of typical salts is exemplified below.

EXAMPLE 70

N-(4-chlorophenyl)-N-[(3-N-methylpyridinium)methyl]-(2-chloroethylamino)carboxamide iodide.

Approximately 1.3 g. of N-(4-chlorophenyl)-N-[(3-pyridyl)methyl]-(2-chloroethylamino)carboxamide, prepared by the procedure of Example 66, was dissolved in diethyl ether and an excess of methyl iodide was added to the reaction mixture. The mixture was stored at room temperature in the dark for about 5 days. The solvent was decanted and the precipitate was triturated with fresh diethyl ether, filtered, washed with diethyl ether and dried in vacuo to yield 1.2 g. of N-(4-chlorophenyl)-N-[(3-N-methylpyridinium)methyl]-(2-chloroethylamino)carboxamide iodide as an oil.

Analysis calculated for $C_{16}H_{18}Cl_2IN_3O$: Theory: C,41.23; H,3.89; N,9.01; Found: C,40.99; H,3.85; N,8.81.

EXAMPLE 71

N-(2,6-dimethylphenyl)-N-[(3-N-ethylpyridinium)methyl]-2,2-dimethylpropanamide iodide Approximately 1.6 g. of N-(2,6-dimethylphenyl)-N-[(3-pyridyl)methyl]-2,2-dimethylpropanamide, prepared by procedure of Example 80, was dissolved in diethyl ether and an excess of ethyl iodide was added. The mixture was held at room temperature in the dark for 7 days. The precipitate was filtered and washed with ether to give N-(2,6-dimethylphenyl)-N-[(3-N-ethylpyridinium)methyl]-2,2-dimethylpropanamide iodide. Yield 500 mg. M.P. 182°–185° C.

Analysis calculated for $C_{21}H_{29}IN_2O$: Theory: C,55.76; H,6.46; N,6.19; Found: C,55.99; H,6.64; N,6.14.

EXAMPLE 72

N-(2,6-diethylphenyl)-N-[(3-N-methylpyridinium)methyl]acetamide iodide was prepared by the method of Example 71. M.P. 180°–182° C.

Analysis calculated for $C_{19}H_{25}IN_2O$: Theory: C,53.78; H,5.94; N,6.60; Found: C,53.71; H,6.00; N,6.40.

EXAMPLE 73

N-(2,6-dimethylphenyl)-N-[1-(3-pyridyl)ethyl]-chloroacetamide hydrochloride

Approximately 1.1 g. of N-(2,6-dimethylphenyl)-N-[1-(3-pyridyl)ethyl]chloroacetamide was dissolved in 100 ml. of a 1:1 v/v mixture of chloroform/diethyl ether. To this solution was added a hydrochloric acid saturated diethyl ether solution. The resulting precipitate was filtered to yield 1.1 g. of N-(2,6-dimethylphenyl)-N-[1-(3-pyridyl)ethyl]chloroacetamide hydrochloride M.P. 182°–185° C.

Analysis calculated for $C_{17}H_{20}Cl_2N_2O$: Theory: C,60.18; H,5.94; N,8.27; Found: C,60.40; H,5.86; N,8.16. The following hydrochloride salts were prepared by the method of Example 73.

EXAMPLE 74

N-(4-chlorophenyl)-N-[(3-pyridyl)methyl]-chloroacetamide hydrochloride M.P. 179°–182° C.

Analysis calculated for $C_{14}H_{13}Cl_3N_2O$: Theory: C,50.71; H,3.95; N,8.45; Found: C,50.94; H,3.71; N,8.15.

EXAMPLE 75

N-(2,6-dimethylphenyl)-N-[(4-pyridyl)methyl]-chloroacetamide hydrochloride M.P. 245° C.

Analysis calculated for $C_{16}H_{18}Cl_2N_2O$: Theory: C,59.09; H,5.58; N,8.61; Found: C,58.84; H,5.30; N,8.32.

EXAMPLE 76

N-(2,6-dimethylphenyl)-N-[(3-pyridyl)methyl]-chloroacetamide hydrochloride M.P. 169°–171° C.

Analysis calculated for $C_{16}H_{18}Cl_2N_2O$: Theory: C,59.09; H,5.58; N,8.61; Found: C,59.29; H,5.52; N,8.70.

Additional examples of the present novel compounds include the following.

EXAMPLE 77

N-(4-chlorophenyl)-N-[(3-pyridyl)methyl]ethylaminothiocarboxamide M.P. 142°–143° C.

Analysis calculated for $C_{15}H_{16}ClN_3S$: Theory: C,58.91; H,5.27; N,13.74; Found: C,58.68; H,5.19; N,13.59.

EXAMPLE 78

N-(2,6-diethylphenyl)-N-[(3-pyridyl)methyl]ethylaminothiocarboxamide M.P. 90°–93° C.

Analysis calculated for $C_{19}H_{25}N_3S$: Theory: C,69.68; H,7.69; N,12.83; Found: C,69.49; H,7.61; N,12.92.

EXAMPLE 79

N-(4-chlorophenyl)-N-[(3-pyridyl)methyl]-2-propenylaminothiocarboxamide M.P. 131°–134° C.

Analysis calculated for $C_{16}H_{16}ClN_3S$: Theory: C,60.46; H,5.07; N,13.22; Found: C,60.25; H,5.24; N,13.04.

EXAMPLE 80

N-(2,6-diethylphenyl)-N-[(3-pyridyl)methyl]heptylaminothiocarboxamide Oil

Analysis calculated for $C_{24}H_{35}N_3S$: Theory: C,72.54; H,8.82; N,10.58; Found: C,71.77; H,7.78; N,10.33.

EXAMPLE 81

N-(2-chlorophenyl)-N-[(3-pyridyl)methyl]ethoxycarbonylaminothiocarboxamide M.P. 110°–112° C.

Analysis calculated for $C_{16}H_{16}ClN_3O_2S$: Theory: C,54.93; H,4.61; N,12.01; Found: C,54.71; H,4.76; N,11.83.

EXAMPLE 82

N-(2,6-dimethylphenyl)-N-[(4-pyridyl)methyl]-butanamide Oil

Analysis calculated for $C_{18}H_{23}N_2O$: Theory: C,76.56; H,7.85; N,9.97; Found: C,75.00; H,7.82; N,9.25.

EXAMPLE 83

N-[1-(4-fluorophenyl)ethyl]-N-3-pyridyl-α-(n-butylthio)acetamide Oil

Analysis calculated for $C_{19}H_{23}FN_2OS$: Theory: C,65.87; H,6.69; N,8.09; Found: C,65.59; H,6.65; N,7.89.

EXAMPLE 84

N-(3,4-methylenedioxyphenyl)-N-[(3-pyridyl)methyl]-2,2-dimethylpropanamide M.P. 101°–102° C.

Analysis calculated for $C_{18}H_{20}N_2O_3$: Theory: C,69.21; H,6.45; N,8.97; Found: C,69.01; H,6.50; N,9.00.

EXAMPLE 85

N,N-bis[(3-pyridyl)methyl]-α,α,α-trifluoroacetamide M.P. 52°–53° C.

EXAMPLE 86

N-[(3-pyridyl)methyl]-N-(4-fluorophenyl)acetamide Oil

EXAMPLE 87

N-[(3-pyridyl)methyl]-N-(2,6-dichlorophenyl)-2,2-dimethylpropanamide M.P. 100°–103° C.

Analysis calculated for $C_{17}H_{18}Cl_2N_2O$: Theory: C,60.54; H,5.38; N,8.31, Found: C,60.50; H,5.35; N,8.22.

EXAMPLE 88

N-[(3-pyridyl)methyl]-N-(2,4-dichlorophenyl)-2-methylpropanamide

Oil

Analysis calculated for $C_{16}H_{16}Cl_2N_2O$: Theory: C,59.46; H,4.99; N,8.67; Found: C,59.51; H,5.05; N,8.58.

EXAMPLE 89

N-[(3-pyridyl)methyl]-N-[2-(1,1,2,2-tetrafluoroethoxy)phenyl]-2,2-dimethylpropanamide Oil Analysis calculated for $C_{19}H_{20}F_4N_2O_2$: Theory: C,59.37; H,5.24; N,7.29; Found: C,59.28; H,5.19; N,7.11.

The N,N-disubstituted carboxamide derivatives of the present invention have been found to display both pre- and postemergent selective herbicidal activity against a variety of weed species, and are thus useful in controlling and inhibiting the growth of broadleaf and grassy weeds in crops such as cereal grains and the like. A herbicidal method employing the compounds of the invention is thus provided as another embodiment of the invention. To control the growth of unwanted vegetation, the compounds can be applied directly to young plants in a growth inhibiting amount, but are preferably applied to the soil prior to the emergence of the plants. The compounds may be either incorporated into the soil, by using a conventional disc or harrow prior to planting the seeds of the desired crop species, such as soybeans, corn and the like, or by surface applying the compounds to the soil prior to substantial plant emergence. In this latter procedure the compounds are merely permitted to leach into the soil, for example with the assistance of rainfall. While the compounds of the present invention display activity against a wide variety of weed species, they are most effective against lambsquarter, pigweed, ragweed, jimsonweed and morning-glory. The compounds are selective herbicides in that they are safe for use in desired crops such as corn, wheat, soybeans, rice and the like.

The term "growth inhibiting amount", as used herein, refers to an amount of a compound of the present invention which either kills or stunts the growth of the weed species for which control is desired. This amount will generally be from about 0.05 to about 15.0 pounds of N,N-disubstituted carboxamide derivative per acre (about 0.056 to about 16.8 kg./ha.). The compounds are more preferably applied at rates of about 0.25 to about 8.0 pounds per acre (about 0.28 to about 8.96 kg./ha.). The exact concentration of compound required varies with the weed species to be controlled, type of formulation, soil condition, climate, and related factors.

The compounds of this invention are also useful as aquatic herbicides. When controlling plant growth in ponds, lakes, streams and the like, the compounds will be added to the water in the area in which the plants are growing, or if desired, directly to the plants, at the rate of about 0.25 to about 8.0 lbs./acre, ideally about 1 to about 5 lbs./acre.

The terrestrial herbicidal activity of representative compounds of the present invention is demonstrated by the following experiments.

Experiment 1

The compounds provided by this invention have been evaluated in standard greenhouse screens designed to demonstrate herbicidal activity. An initial herbicide test was run at a compound concentration of 15 lbs./acre (16.8 kg./ha.). In this test, a standard sand:soil mixture (1:1) was sterilized at approximately 245° F. for 24 hours in an autoclave. Following sterilization, the standard soil mixture was added to separate containers. Tomato, large crabgrass and pigweed seeds were planted in the soil by row. Each container was then fertilized with a 23-21-17 fertilizer mixture four days before treatment with a compound of this invention.

The test compounds were formulated for application by dissolving 20 mg. of the compound into 2 ml. of a solvent prepared by placing 1.174 g. of Toximul R and 0.783 g. of Toximul S (proprietary blends of anionic and nonionic surfactants manufactured by Stepan Chemical Company, Northfield, Ill.) into 100 ml. of acetone and 100 ml. of ethyl alcohol. The solvent/compound solution was diluted to 8 ml. with deionized water. The solution was applied postemergence to some planted containers and preemergence to others using a modified DeVilbiss atomizer. Preemergence treatment was made one day after planting, while postemergence treatment was made 11 to 13 days after planting.

Following application of the test compound the containers were moved to the greenhouse and watered as necessary. Observations for plant injury were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. Also, the various types of injury of each test species were coded as follows:

A=abscission of leaves
B=burned
C=chlorosis
D=death
E=epinasty
F=formation effects
G=dark green
I=increased plant growth
L=local necrosis
N=no germination
P=purple pigmentation
R=reduced germination
S=stunting
U=unclassified injury Table I presents the herbicidal activity of typical N,N-disubstituted carboxamide derivatives of the present invention when evaluated in the herbicide test described above.

TABLE I

| | Herbicidal Activity at 15 lbs./acre (16.8 kg./ha.) | | | | | |
|---|---|---|---|---|---|---|
| | Preemergence | | | Postemergence | | |
| Example No. of Compound Tested | Tomato | Large Crab-grass | Pig-weed | To-mato | Large Crab-grass | Pig-Weed |
| 1 | 4RS | 4RS | 3RS | 1 | 2B | 2B |
| 2 | 1 | 3RS | 1 | 2CFS | 2BS | 3BS |
| 3 | 1 | 4RS | 4RS | 3CBS | 3BS | 3BS |
| 4 | 1 | 5N | 2S | 3CBS | 3BS | 3BS |
| 5 | 5N | 5N | 5N | 4BS | 5D | 3BS |
| 6 | 2RS | 5N | 2FS | 2CS | 4BS | 3BS |
| 7 | 1 | 2RS | 2S | 2S | 2BS | 2BS |
| 8 | 1 | 2RS | 2RS | 4BS | 4BS | 3BS |
| 9 | 1 | 3RS | 2RS | 2CBS | 2BS | 2BS |
| 10 | 1 | 3RS | 1 | 1 | 4BS | 2BS |
| 11 | 2S | 5N | 3RS | 2CS | 4BS | 4BS |

TABLE I-continued

| Example No. of Compound Tested | Preemergence Tomato | Preemergence Large Crabgrass | Preemergence Pigweed | Postemergence Tomato | Postemergence Large Crabgrass | Postemergence Pigweed |
|---|---|---|---|---|---|---|
| 12 | 4RS | 4SF | 4SF | 4CBS | 4CBS | 4CBS |
| 13 | 1 | 1 | 1 | 1 | 3BS | 3BS |
| 14 | 1 | 3RS | 1 | 2CBS | 2CBS | 3 |
| 15 | 1 | 1 | 1 | 1 | 1 | 1 |
| 16 | 1 | 1 | 1 | 1 | 1 | 1 |
| 17 | 1 | 1 | 1 | 2FS | 2BS | 1 |
| 19 | 1 | 2RS | 2RS | 1 | 2BS | 2BS |
| 20 | 1 | 2RS | 1 | 1 | 3BS | 2BS |
| 21 | 1 | 1 | 1 | 1 | 1 | 1 |
| 22 | 1 | 1 | 1 | 1 | 1 | 1 |
| 23 | 1 | 1 | 1 | 1 | 1 | 1 |
| 24 | 1 | 1 | 1 | 1 | 1 | 1 |
| 25 | 1 | 1 | 1 | 2S | 1 | 2S |
| 26 | 1 | 1 | 1 | 1 | 1 | 1 |
| 27 | 1 | 1 | 1 | 1 | 1 | 1 |
| 28 | 1 | 1 | 1 | 1 | 1 | 1 |
| 29 | 5N | 5N | 1 | 4BS | 4BS | 5D |
| 30 | 1 | 4RS | 2S | 5D | 2BS | 5D |
| 32 | 1 | 3RS | 1 | 1 | 1 | 1 |
| 33 | 1 | 1 | 1 | 1 | 1 | 1 |
| 34 | 2S | 4RS | 4RS | 2S | 2BS | 2BS |
| 35 | 3RS | 4CS | 4RS | 4FS | 3BS | 5D |
| 36 | 1 | 3RS | 2RS | 1 | 3BS | 2BS |
| 37 | 2S | 4RS | 4RS | 5D | 5D | 5D |
| 38 | 1 | 1 | 1 | 1 | 2BS | 1 |
| 39 | 1 | 1 | 1 | 1 | 1 | 1 |
| 40 | 1 | 2RS | 1 | 1 | 2BS | 1 |
| 41 | 5N | 4RS | 4RS | 1 | 2BS | 1 |
| 42 | 1 | 3RS | 2RS | 1 | 2BS | 2BS |
| 43 | 1 | 2S | 1 | 3FS | 1 | 1 |
| 44 | 2S | 4RS | 1 | 4FS | 4BS | 4BS |
| 45 | 1 | 4RS | 1 | 2FS | 4BS | 5D |
| 46 | 1 | 1 | 1 | 4CFS | 4BS | 4BS |
| 47 | 5N | 5N | 5N | 4CFS | 4BS | 4BS |
| 48 | 5D | 5N | 4RS | 5D | 4BS | 4BS |
| 49 | 1 | 2RS | 1 | 3BS | 2BS | 2BS |
| 50 | 1 | 5N | 4RS | 3FS | 4BS | 4BS |
| 51 | 3RS | 5N | 3RS | 5D | 4BS | 5D |
| 52 | 1 | 4RS | 2S | 2FS | 4BS | 4BS |
| 53 | 2RS | 4RS | 1 | 1 | 2BS | 1 |
| 58 | 1 | 1 | 1 | 5D | 4BS | 5D |
| 59 | 1 | 1 | 1 | 1 | 2BS | 2BS |
| 61 | 3RS | 1 | 1 | 1 | 3BS | 2BS |
| 63 | 1 | 1 | 1 | 2FS | 1 | 1 |
| 65 | 1 | 4RS | 5N | 5D | 5D | 5D |
| 66 | 1 | 1 | 1 | 1 | 1 | 1 |
| 67 | 1 | 2RS | 2RS | 4BS | 4CBS | 3CBS |
| 68 | 1 | 1 | 1 | 1 | 1 | 1 |
| 70 | 1 | 1 | 1 | 1 | 1 | 1 |
| 71 | 1 | 1 | 1 | 1 | 2BS | 1 |
| 72 | 1 | 1 | 1 | 1 | 1 | 1 |
| 73 | 2S | 5N | 4RS | 2S | 3BS | 1 |
| 74 | 1 | 1 | 1 | 1 | 2BS | 1 |
| 75 | 1 | 1 | 1 | 1 | 1 | 1 |
| 76 | 2S | 5N | 4RS | 1 | 2BS | 2BS |
| 78 | 1 | 1 | 3RS | 1 | 1 | 1 |
| 80 | 1 | 1 | 1 | 1 | 1 | 1 |
| 82 | 1 | 3RS | 2RS | 1 | 3BS | 2BS |
| 83 | 1 | 1 | 1 | 1 | 1 | 1 |

Experiment 2

The herbicidal activity of some of the compounds of the present invention was further evaluated at various application rates in a multiple species greenhouse test. Several additional weed and crop species were utilized to determine the herbicidal activity and selectivity of the test compounds. The compounds were formulated according to the procedure as described above, except that about 4 g. of the compound was dissolved in 100 ml. of the surfactant containing solvent, and about one part of that solution was diluted with 12 parts of water before application to the seed containers. Table II presents preemergence herbicidal test results for the compounds administered at 8 lbs./acre (8.96 kg./ha.) or less, while Table III presents postemergence test data from similar application rates. Blank spaces in the Tables means that the compound was not evaluated against the particular plant species.

TABLE II

| | | Crops | | | | | | | | | Preemergence Weeds | | | | | | | | | |
|---|---|---|---|---|---|---|---|---|---|---|---|---|---|---|---|---|---|---|---|---|
| Example No. of Compound Tested | Rate of Appln. lbs./acre (kg./ha.) | Corn | Cotton | Soybean | Wheat | Alfalfa | Sugar Beet | Rice | Cucumber | Tomato | Barnyard Grass | Lambs-quarter | Large Crab-grass | Mustard | Pigweed | Foxtail | Wild Oat | Velvet-leaf | Jimson-weed | Morning-glory | Zinnia |
| 4 | 8.0 (8.96) | 1 | 1 | 1 | 1 | 1 | 1 | 1 | 1 | 1 | 2 | 1 | 4 | 2 | 3 | 4 | — | 2 | 4 | 1 | 1 |
| | 4.0 (4.48) | 1 | 1 | 1 | 1 | 1 | 1 | 1 | 1 | 1 | 1 | 1 | 2 | 2 | 3 | 2 | — | 2 | 4 | 3 | 5 |
| | 2.0 (2.24) | 1 | 1 | 1 | 1 | 1 | 1 | 1 | 1 | 1 | 1 | 2 | 2 | 2 | 5 | 3 | — | 1 | 3 | 2 | 3 |
| | 1.0 (1.12) | 1 | 1 | 1 | 1 | 1 | 1 | 1 | 1 | 1 | 1 | — | 2 | 2 | 5 | 1 | — | 1 | 1 | 1 | 1 |
| | 0.5 (0.56) | 1 | 1 | 1 | 1 | 1 | 1 | 1 | 1 | 1 | 1 | — | 2 | 1 | 1 | 1 | — | 1 | 1 | 1 | 1 |
| | 0.25 (0.28) | 1 | 1 | 1 | 1 | 1 | 1 | 1 | 1 | 1 | 1 | — | 1 | — | 1 | 1 | — | 1 | 1 | 2 | 1 |
| 5 | 8.0 (8.96) | 1 | 1 | 1 | 1 | 1 | 1 | 1 | 1 | 1 | 5 | 1 | 4 | — | 2 | 4 | — | 3 | 1 | 2 | 1 |
| | 4.0 (4.48) | 1 | 1 | 1 | 1 | 1 | 1 | 1 | 1 | 1 | 4 | 1 | 4 | — | 1 | 4 | — | 1 | 1 | 1 | 3 |
| | 2.0 (2.24) | 1 | 1 | 1 | 1 | 1 | 1 | 1 | 1 | 1 | 2 | 1 | 2 | — | 1 | 2 | — | 1 | 1 | 1 | 1 |
| | 1.0 (1.12) | 1 | 1 | 1 | 1 | 1 | 1 | 1 | 1 | 1 | 1 | — | 2 | — | 1 | 1 | — | — | — | — | 1 |
| 6 | 8.0 (8.96) | 1 | 1 | 1 | 1 | 1 | 1 | 1 | 1 | 1 | 2 | 1 | 4 | 2 | 3 | 4 | 1 | 2 | 4 | 3 | 5 |
| | 4.0 (4.48) | 1 | 1 | 1 | 1 | 1 | 1 | 1 | 1 | 1 | 1 | 2 | 2 | 2 | 3 | 2 | — | 2 | 3 | 2 | 3 |
| | 2.0 (2.24) | 1 | 1 | 1 | 1 | 1 | 1 | 1 | 1 | 1 | 1 | 1 | 2 | 2 | 5 | 3 | — | 1 | 1 | 1 | 1 |
| | 1.0 (1.12) | 1 | 1 | 1 | 1 | 1 | 1 | 1 | 1 | 1 | 1 | — | 2 | 1 | 2 | 1 | — | 1 | 1 | 1 | 1 |
| | 1.0 (1.12) | 1 | 1 | 1 | 1 | 1 | 1 | 1 | 1 | 1 | — | 2 | 3 | — | 1 | 1 | — | 1 | — | 1 | 1 |
| | 0.5 (0.56) | 1 | 1 | 1 | 1 | 1 | 1 | 1 | 1 | 1 | — | 1 | 1 | — | 1 | 1 | — | 1 | — | 1 | 1 |
| | 0.25(0.28) | 1 | 1 | 1 | 1 | 1 | 1 | 1 | 1 | 1 | — | — | 3 | — | 2 | — | — | — | — | — | — |
| 12 | 8.0 (8.96) | 1 | 1 | — | — | 1 | 1 | 1 | 1 | 1 | 4 | — | 4 | 2 | 3 | 3 | 2 | 1 | — | — | 2 |
| 30 | 8.0 (8.96) | 1 | 1 | — | — | 1 | 1 | 1 | 1 | 1 | — | — | 4 | — | 3 | 3 | — | 1 | 1 | — | 3 |
| 34 | 8.0 (8.96) | 1 | 1 | — | — | 1 | 1 | 1 | 1 | 1 | — | — | 3 | — | 3 | 1 | — | 1 | 1 | — | — |
| 35 | 8.0 (8.96) | 1 | 1 | — | 1 | 1 | 1 | 1 | 1 | 1 | 1 | 3 | 4 | — | 1 | 4 | 1 | 1 | 1 | 2 | 2 |
| 37 | 4.0 (4.48) | 1 | 1 | — | 1 | 1 | 1 | 1 | 1 | 1 | 1 | 1 | 1 | — | — | 1 | — | 1 | 1 | 1 | 1 |
| | 2.0 (2.24) | 1 | 1 | — | 1 | 1 | 1 | 1 | 1 | 1 | 1 | 1 | 1 | — | 2 | 1 | — | 1 | — | 1 | 1 |
| | 1.0 (1.12) | 1 | 1 | — | 1 | 1 | 1 | 1 | 1 | 1 | 1 | 1 | 1 | — | 1 | — | — | — | — | — | — |
| 41 | 8.0 (8.96) | 2 | 1 | — | — | 1 | 1 | 1 | 1 | 4 | 4 | — | 4 | 2 | 2 | 2 | — | 2 | — | 2 | 2 |
| 44 | 8.0 (8.96) | 2 | 1 | — | — | 1 | 1 | 1 | 2 | 3 | 3 | — | 5 | 3 | 3 | 5 | 3 | 2 | 4 | 2 | 3 |
| | 4.0 (4.48) | 3 | 5 | 3 | 1 | 1 | 3 | 4 | 2 | 4 | 4 | — | 5 | 3 | 4 | 5 | 1 | 1 | 4 | 4 | 2 |
| | 2.0 (2.24) | 2 | 5 | 5 | 1 | 1 | 2 | — | 1 | 3 | 3 | — | 5 | 2 | 2 | 4 | — | 1 | 1 | 1 | 1 |
| | 1.0 (1.12) | 3 | 3 | 3 | 1 | 1 | 1 | 2 | 1 | 4 | 1 | — | 4 | 2 | 1 | 4 | — | 1 | 2 | — | 1 |
| | 1.0 (1.12) | 1 | 1 | 2 | 2 | 2 | 1 | — | 1 | 1 | 1 | — | 1 | 2 | 3 | 3 | 1 | 1 | — | 1 | — |
| | 0.5 (0.56) | 1 | 1 | 2 | 1 | 2 | 1 | — | 1 | 1 | 1 | — | 4 | 2 | 2 | 3 | — | 1 | — | 1 | — |
| | 0.25(0.28) | 1 | 1 | 1 | 1 | 1 | 1 | — | 1 | 1 | 1 | — | 4 | 2 | 2 | 3 | — | 1 | — | — | — |
| 45 | 8.0 (8.96) | 1 | 1 | — | — | 1 | 1 | — | 1 | 1 | — | 5 | 4 | 3 | 5 | 4 | 3 | 3 | — | 2 | 2 |
| 47 | 8.0 (8.96) | 1 | 1 | — | — | 1 | 1 | — | 1 | 1 | — | — | 5 | — | 1 | 5 | 1 | 1 | 1 | 4 | 1 |
| | 4.0 (4.48) | 1 | — | — | — | 1 | 1 | — | 1 | 1 | — | — | 1 | 1 | 1 | 1 | — | — | — | 1 | 1 |
| | 2.0 (2.24) | 1 | 1 | — | — | 1 | 1 | — | 1 | 1 | — | — | 2 | — | 1 | 2 | — | 3 | — | — | 2 |
| | 1.0 (1.12) | 1 | 1 | — | — | 1 | 1 | — | 1 | 1 | — | — | 1 | — | 1 | — | — | 1 | — | — | 1 |
| | 0.5 (0.56) | 1 | 1 | — | — | 1 | 1 | — | 1 | 1 | — | — | 1 | — | 1 | — | — | — | — | — | 1 |
| 48 | 8.0 (8.96) | 1 | 1 | 1 | 1 | 1 | 1 | — | 1 | 1 | 3 | 3 | 5 | 2 | 4 | 4 | 1 | 3 | — | — | 2 |
| 50 | 8.0 (8.96) | 2 | 2 | 2 | 1 | 1 | 2 | — | 1 | 1 | 3 | 2 | 5 | 2 | 2 | 4 | — | 1 | — | — | 2 |
| | 4.0 (4.48) | 2 | 2 | 2 | — | 2 | 1 | — | 1 | 1 | 1 | 1 | 4 | 1 | 3 | 3 | — | 3 | — | 2 | 2 |
| | 2.0 (2.24) | 1 | 1 | — | — | 1 | — | — | 1 | 1 | — | — | 4 | — | 1 | 3 | — | 3 | — | 1 | 1 |
| | 1.0 (1.12) | 1 | — | — | — | 1 | — | — | 1 | 1 | — | — | 2 | — | 1 | 1 | — | — | — | — | — |
| 51 | 8.0 (8.96) | 1 | 3 | 2 | 1 | 1 | 2 | 1 | 1 | 3 | 3 | 1 | 4 | — | 3 | 4 | 1 | 2 | 2 | 2 | 2 |
| | 4.0 (4.48) | 1 | 1 | 1 | — | 1 | 1 | 1 | 2 | 1 | 2 | — | 2 | — | 2 | 4 | — | 2 | — | 1 | 2 |
| | 2.0 (2.24) | 1 | — | — | — | — | — | — | — | — | — | — | — | — | 1 | 3 | — | 1 | — | — | 1 |

TABLE II-continued

| | | Crops | | | | | | | | | Preemergence Weeds | | | | | | | | | | |
|---|---|---|---|---|---|---|---|---|---|---|---|---|---|---|---|---|---|---|---|---|---|
| Example No. of Compound Tested | Rate of Appln. lbs./acre (kg./ha.) | Corn | Cotton | Soybean | Wheat | Alfalfa | Sugar Beet | Rice | Cucumber | Tomato | Barnyard Grass | Lambs-quarter | Large Crab-grass | Mustard | Pigweed | Foxtail | Wild Oat | Velvet-leaf | Jimson-weed | Morning-glory | Zinnia |
| 52 | 1.0 (1.12) | 1 | — | — | — | — | — | — | — | — | — | — | — | — | — | — | — | — | — | — | — |
|    | 8.0 (8.96) | 3 | 1 | 1 | 1 | — | 2 | 2 | 1 | 2 | 2 | 3 | 4 | 3 | 2 | 4 | 1 | 2 | 1 | — | — |
|    | 4.0 (4.48) | 2 | 1 | 1 | 1 | — | 2 | 1 | 1 | 3 | 2 | 4 | 3 | 1 | 2 | 4 | 1 | 1 | 1 | — | — |
|    | 2.0 (2.24) | 2 | 1 | 1 | 1 | — | 1 | — | 1 | 1 | — | 1 | 1 | — | 3 | 4 | — | — | — | — | — |
|    | 1.0 (1.12) | 1 | — | — | — | — | — | — | 1 | — | — | — | 1 | — | 2 | 3 | — | — | — | — | 1 |
| 53 | 8.0 (8.96) | 1 | 1 | 1 | 1 | 1 | — | — | 1 | 1 | 1 | — | 3 | 1 | 1 | 4 | — | 2 | — | — | 1 |
|    | 4.0 (4.48) | 1 | 1 | 1 | — | 1 | — | — | 1 | 1 | 1 | 1 | 3 | 1 | — | 4 | — | 1 | — | — | 1 |
|    | 2.0 (2.24) | 1 | 1 | 1 | — | — | — | — | — | — | — | — | — | — | — | 1 | — | — | — | — | 1 |
|    | 1.0 (1.12) | 1 | — | — | — | — | — | — | 1 | — | — | — | — | — | — | 1 | — | — | — | — | 3 |
| 65 | 8.0 (8.96) | 1 | — | — | — | — | — | — | — | — | — | — | 1 | — | — | 1 | — | — | — | — | 2 |
| 67 | 8.0 (8.96) | 3 | — | — | — | — | — | — | 1 | — | — | — | 1 | — | — | 1 | — | — | — | — | 2 |
|    | 4.0 (4.48) | 4 | 2 | 2 | 2 | 1 | 2 | 5 | 1 | 2 | 5 | 5 | 4 | 1 | 4 | 5 | 4 | 2 | 2 | 2 | 2 |
|    | 2.0 (2.24) | 3 | 2 | 2 | 2 | — | 1 | 5 | 1 | 1 | 5 | 5 | 5 | 1 | 3 | 5 | 4 | 3 | 1 | 2 | 1 |
|    | 1.0 (1.12) | 1 | 2 | 3 | 2 | 2 | 1 | 5 | 3 | 2 | 4 | 2 | 4 | 1 | 2 | 5 | 2 | 2 | 1 | 2 | — |
|    | 1.0 (1.12) | 3 | 4 | 2 | 1 | 1 | 1 | 4 | 1 | — | 4 | 4 | 4 | — | 1 | 4 | 1 | 3 | 1 | 1 | 1 |
|    | 0.5 (0.56) | 1 | 1 | 1 | 1 | 1 | 1 | 1 | 1 | 2 | 4 | 1 | 3 | 2 | 1 | 3 | 2 | 1 | 1 | 2 | 1 |
|    | 0.25 (0.28) | 4 | 1 | 1 | 1 | 1 | 1 | 1 | 1 | 1 | 4 | 1 | 1 | 2 | — | 3 | 3 | — | — | — | 2 |
| 76 | 8.0 (8.96) | 1 | — | — | 1 | 1 | 2 | 1 | 1 | 1 | 3 | 2 | 4 | 2 | 4 | 4 | 3 | 2 | 1 | 2 | 2 |
|    | 4.0 (4.48) | 3 | 1 | 1 | 2 | 2 | 1 | 3 | 1 | 3 | 4 | 5 | 5 | 1 | 3 | 4 | 4 | 3 | — | 2 | 2 |
|    | 4.0 (4.48) | 2 | 1 | 1 | 2 | 1 | 1 | 3 | 1 | 2 | 3 | 2 | 4 | 2 | 2 | 3 | 1 | 2 | — | 1 | 1 |
|    | 2.0 (2.24) | 2 | 1 | 2 | 2 | 1 | 1 | 1 | 1 | 2 | 4 | 4 | 4 | 3 | 3 | 3 | 4 | 1 | 1 | 1 | — |
|    | 2.0 (2.24) | 1 | 1 | 1 | 1 | 1 | 1 | 1 | 1 | 1 | 3 | 3 | 4 | 2 | 3 | 3 | 1 | — | 1 | 2 | 1 |
|    | 1.0 (1.12) | 1 | 1 | 1 | 1 | 1 | 1 | 1 | 1 | 1 | 3 | 1 | 3 | 1 | 2 | 4 | 2 | 2 | — | 1 | 1 |
|    | 1.0 (1.12) | 1 | 1 | 1 | 1 | 1 | 1 | 1 | 1 | 1 | 3 | 5 | 3 | 1 | — | 3 | 3 | 1 | 1 | 1 | 2 |
|    | 1.0 (1.12) | 1 | 1 | 1 | 1 | 1 | 1 | — | 1 | 1 | 4 | 1 | 3 | 1 | 1 | 4 | 1 | 2 | — | 1 | 2 |
|    | 0.5 (0.56) | 1 | 1 | 1 | 1 | 1 | 1 | 1 | 1 | 1 | 3 | — | 3 | — | — | 1 | 2 | 1 | — | — | 2 |
|    | 0.25 (0.28) | 1 | 1 | 1 | 1 | 1 | 1 | 1 | 1 | 1 | 4 | 1 | 5 | 1 | 1 | 4 | — | 1 | 1 | 1 | 1 |
| 89 | 8.0 (8.96) | 1 | 1 | 1 | 1 | 1 | 2 | 1 | 1 | 1 | 4 | 2 | 4 | 1 | 1 | 4 | 2 | 1 | — | 1 | 1 |
|    | 4.0 (4.48) | 1 | 1 | 1 | 1 | 1 | 1 | 1 | 1 | 1 | 2 | 1 | 3 | 1 | 1 | 1 | 1 | 1 | 1 | 1 | 1 |
|    | 2.0 (2.24) | 1 | 1 | 1 | 1 | 1 | 2 | — | 1 | 1 | 2 | 1 | 4 | 1 | 1 | 4 | 1 | 1 | — | 1 | 1 |
|    | 1.0 (1.12) | 1 | 1 | 1 | 1 | 1 | — | — | 1 | 1 | 1 | — | — | — | — | 2 | — | — | — | — | — |

TABLE III

Postemergence

| Example No. of Compound Tested | Rate of Appln. lbs./acre (kg./ha.) | Corn | Tomato | Large Crabgrass | Pigweed | Foxtail | Velvet-leaf | Morning-glory | Zinnia | Barnyard Grass | Mustard | Wild Oat |
|---|---|---|---|---|---|---|---|---|---|---|---|---|
| 4 | 8.0 (8.96) | 2 | | 3 | 4 | 2 | 3 | 3 | 3 | | | |
| 5 | 8.0 (8.96) | 1 | | 1 | 3 | 1 | 3 | 3 | 3 | | | |
| 6 | 8.0 (8.96) | 2 | | 3 | 4 | 2 | 3 | 3 | 3 | | | |
| 12 | 8.0 (8.96) | 2 | | 2 | 3 | 1 | 2 | 2 | 3 | | | |
| 30 | 8.0 (8.96) | 2 | | 3 | 4 | 1 | 3 | 3 | 3 | | | |
| 35 | 8.0 (8.96) | 1 | | 2 | 5 | 2 | 3 | 4 | 4 | | | |
|  | 4.0 (4.48) | | 2 | 2 | 3 | 2 | 1 | 3 | 3 | 2 | 3 | 2 |
|  | 2.0 (2.24) | | 2 | 1 | 3 | 1 | 1 | 3 | 3 | 1 | 2 | 2 |
|  | 1.0 (1.12) | | 1 | 1 | 3 | 1 | 1 | 3 | 3 | 1 | 2 | 1 |
| 37 | 8.0 (8.96) | 2 | | 2 | 2 | 1 | 3 | 3 | 3 | | | |
| 44 | 8.0 (8.96) | 2 | | 2 | 2 | 2 | 2 | 2 | 2 | | | |
| 45 | 8.0 (8.96) | 3 | | 2 | 4 | 2 | 3 | 2 | 3 | | | |
| 46 | 8.0 (8.96) | 2 | | 2 | 2 | 2 | 3 | 2 | 2 | | | |
| 47 | 8.0 (8.96) | 2 | | 2 | 2 | 2 | 2 | 3 | 2 | | | |
| 48 | 8.0 (8.96) | 1 | | 1 | 1 | 2 | 2 | 1 | 2 | | | |
| 50 | 8.0 (8.96) | 1 | | 4 | 3 | 3 | 3 | 2 | 3 | | | |
| 51 | 8.0 (8.96) | 2 | | 2 | 3 | 2 | 3 | 2 | 2 | | | |
| 52 | 8.0 (8.96) | 2 | | 3 | 4 | 2 | 2 | 1 | 2 | | | |
| 58 | 8.0 (8.96) | 1 | | 1 | 1 | 1 | 1 | 2 | 3 | | | |
| 65 | 8.0 (8.96) | 1 | | 2 | 2 | 2 | 3 | 2 | 3 | | | |
| 67 | 8.0 (8.96) | 1 | | 2 | 4 | 3 | 1 | 2 | 2 | | | |
| 76 | 1.0 (1.12) | | 1 | 3 | 1 | 3 | 1 | 1 | 1 | 3 | 1 | 3 |
|  | 0.5 (0.56) | | 1 | 1 | 1 | 1 | 1 | 1 | 1 | 1 | 1 | 1 |
|  | 0.25 (0.28) | | 1 | 1 | 1 | 1 | 1 | 1 | 1 | 1 | 1 | 1 |
| 89 | 8.0 (8.96) | | 2 | 3 | 2 | 2 | 3 | 2 | 1 | 2 | 3 | 2 |

As noted above the compounds of this invention have also displayed activity in the regulation of aquatic plant growth. The concentration of compound present in the body of water to be treated depends on the effect desired and plant species to be treated. When the compounds of the present invention are added to the water containing submerged and floating aquatic plants for which control is desired, a concentration range of from about 0.10 to about 10 ppm (parts per million) of the active compound is desired. It is, of course, apparent that higher or lower concentrations can be employed depending on the plant species to be controlled, the temperature, shape and type of the body of water to be treated. At higher water temperatures, for example, less compound is generally required for a given degree of control than is needed at lower temperatures.

The following method was used in the laboratory to evaluate the aquatic growth regulating properties of the compounds disclosed herein.

Experiment 3

The compounds for this test were formulated in the following manner. Twenty milligrams of test compound was weighed into a 12 ml. disposable vial. To the vial containing the compound was added 1 ml. of acetone and 9 ml. of aqueous 0.1 percent Tween 80 (polyoxyethylene sorbitan monooleate). This solution was then diluted with appropriate volumes of water to obtain solutions containing 10, 1, 0.5 and 0.25 ppm of test compound.

Terminal pieces of Florida elodea, *Hydrilla verticillata* (L.F.), (hereinafter identified as hydrilla) 10 cm. long, without branching, were prepared for testing. Three such cuttings were placed in each plastic container holding 785 ml. of water containing the formulated test compound and 3 ml. of Hoagland's nutrient solution. Three 10 cm. cuttings of hydrilla were placed in each of several untreated control containers of water. To the water in each control container there was also added the amount of solvent used to formulate the test compound.

After a period of two to three weeks, measurements were made to determine the total length of each plant. An average total growth was obtained by dividing the total combined lengths by the number of replicates. By subtracting 10 cm. from the average total length, the average increase in growth was obtained. This difference was divided by the average increase in length of the plants in the solvent controls (SC) and the quotient multiplied by 100 to give a percent inhibition, as illustrated below:

$$\frac{\text{Total combined length of Replicates}}{\text{Number of Replicates}} = \text{Average Length}$$

$$\text{Avg. Length} - 10 \text{ cm.} = \text{Avg. Increased Growth}$$

$$\left[1 - \frac{\text{Avg. Increased Growth}}{\text{Avg. Increased Growth } SC}\right] \times 100 = \% \text{ Inhibition}$$

The results of the tests, run at the reported concentration levels in ppm of compound, and observed at the end of three weeks, are set forth in Table IV which follows. In the Table, each compound evaluated in this experiment is identified by the number of the operating example describing its preparation.

TABLE IV

AQUATIC GROWTH REGULATOR ACTIVITY

| Example No. of Compound Tested | Approximate % Growth Inhibition of Hydrilla at Indicated Test Concentration | | | |
|---|---|---|---|---|
|  | 10 ppm | 1 ppm | 0.5 ppm | 0.25 ppm |
| 1 | 95 | 76 | 57 | 41 |
| 2 | 94 | 35 | 27 | 23 |
| 3 | 94 | 9 | 2 | 28 |
| 4 | 90 | 32 | 31 | 27 |
| 5 | 94 | 74 | 63 | 53 |
| 6 | 98 | 31 | 21 | 37 |
| 7 | 96 | — | — | — |

TABLE IV-continued

AQUATIC GROWTH REGULATOR ACTIVITY

| Example No. of Compound Tested | Approximate % Growth Inhibition of Hydrilla at Indicated Test Concentration | | | |
|---|---|---|---|---|
| | 10 ppm | 1 ppm | 0.5 ppm | 0.25 ppm |
| 8 | 98 | 13 | 4 | 15 |
| 9 | 79 | 31 | 35 | 19 |
| 10 | 94 | 19 | 12 | 9 |
| 11 | 97 | 66 | 48 | 42 |
| 12 | 59 | 18 | −1 | −18 |
| 13 | 96 | 40 | 20 | 15 |
| 14 | 95 | — | — | — |
| 15 | 73 | 8 | 2 | −6 |
| 16 | 78 | — | — | — |
| 17 | 94 | −1 | −16 | −1 |
| 18 | 83 | 5 | −4 | −10 |
| 19 | 54 | — | — | — |
| 20 | 73 | −1 | 8 | 10 |
| 21 | 27 | — | — | — |
| 22 | 55 | −14 | −9 | −5 |
| 23 | 42 | — | — | — |
| 24 | 44 | — | — | — |
| 25 | 23 | — | — | — |
| 26 | 88 | — | — | — |
| 27 | 50 | 25 | 9 | 5 |
| 28 | 62 | — | — | — |
| 29 | 96 | — | — | — |
| 30 | 92 | 81 | 67 | 57 |
| 31 | 92 | — | — | — |
| 32 | 87 | 49 | 42 | 41 |
| 33 | 59 | 2 | 10 | −4 |
| 34 | 90 | 69 | 70 | 57 |
| 35 | 87 | 33 | 28 | 23 |
| 36 | 70 | −3 | −10 | 6 |
| 37 | 77 | 29 | 7 | −3 |
| 38 | 42 | — | — | — |
| 39 | 61 | −16 | −2 | −2 |
| 40 | 76 | — | — | — |
| 41 | 85 | 5 | 5 | 1 |
| 42 | 93 | 36 | 21 | 25 |
| 43 | 87 | 12 | 9 | 5 |
| 44 | 95 | 41 | 28 | 25 |
| 45 | 96 | 9 | 15 | 9 |
| 46 | 96 | −3 | −12 | 10 |
| 47 | 95 | 16 | 13 | −4 |
| 49 | 87 | 12 | 6 | 34 |
| 50 | 95 | 82 | 83 | 86 |
| 51 | 94 | — | — | — |
| 52 | 81 | 53 | 34 | 24 |
| 53 | 97 | 55 | 44 | 34 |
| 58 | 36 | −10 | 3 | 1 |
| 61 | 95 | 35 | 13 | −4 |
| 63 | 92 | 45 | 5 | −3 |
| 65 | 94 | 17 | 10 | 9 |
| 66 | 90 | −12 | −11 | 8 |
| 67 | 84 | — | — | — |
| 68 | 71 | −18 | −8 | 6 |
| 70 | 0 | — | — | — |
| 71 | −23 | — | — | — |
| 72 | −5 | — | — | — |
| 73 | 91 | — | — | — |
| 74 | 87 | 2 | 10 | 15 |
| 75 | 94 | 60 | 53 | 24 |
| 76 | 91 | 86 | 80 | 69 |
| 78 | 89 | −3 | 4 | 10 |
| 79 | 73 | — | — | — |
| 80 | 82 | 36 | 15 | 20 |
| 81 | 45 | — | — | — |
| 82 | 84 | — | — | — |
| 83 | 97 | 16 | 24 | 7 |
| 84 | 70 | — | — | — |
| 86 | 65 | — | — | — |
| 88 | 93 | 25 | 23 | 7 |
| 89 | 92 | — | — | — |

As is clear from the foregoing test results, the N,N-disubstituted carboxamide derivatives of this invention are valuable in controlling the growth of aquatic vegetation. Typical aquatic plants that can be controlled include hydrilla, naiad, chara, milfoil, duckweed and the like.

The compounds of the present invention have also been found to control plant fungal diseases, particularly powdery mildew. When employed in the treatment of such plant fungal diseases, the compounds are applied to the plants in a disease inhibiting and non-herbicidal amount. The term "disease inhibiting and non-herbicidal amount", as used herein, refers to an amount of a compound of the invention which kills or stunts the plant disease for which control is desired, but is not toxic to the plant. This amount will generally be from about 1 to 1000 ppm, with 10 to 500 ppm being preferred. The exact concentration of compound required varies with the fungal disease to be controlled, the type formulation employed, the particular plant species, climate conditions and the like.

Experiment 4

The fungicidal activity of compounds of this invention was determined in an initial screen run with a test compound concentration of 400 ppm. The test compounds were formulated for application by dissolving 48 mg. of the compound in 1.2 ml. of solvent. The solvent was prepared by placing 100 ml. of Tween 20 into 500 ml. of acetone and 500 ml. of ethyl alcohol. After mixing, the mixture was allowed to stand overnight and then was diluted to 120 ml. with deionized water containing Dow Corning Antifoam C Emulsion (one drop per two liters).

The formulated test compounds were foliar applied to plants using a hand held DeVilbiss spray gun operating at 40 psi. Single pots of bean plants were placed on raised, revolving pedestals in a ventilated exhaust chamber. As the spray was delivered, the pedestals rotated to expose all plant surfaces to the spray pattern. The spray was applied until the solution began to run off the leaves.

One day after treatment, all bean plants were inoculated with the powdery mildew pathogen (*Erysiphe polygoni*). Inoculation was performed by shaking the spores from other bean plants, heavily infested with powdery mildew, above the test plants.

The effectiveness of test compounds in controlling powdery mildew disease was rated on a scale of 1 to 5. On this scale "1" indicates severe disease (or no control), "2" is moderate disease, "3" is slight disease, "4" is very slight disease and "5" indicates no disease or 100% control. A phytotoxicity rating was also recorded, again using a scale from 1 to 5, where 1 indicates no toxicity and 5 indicates death to the plant. Finally, where phytotoxicity was present, a letter code was given to indicate the type of injury caused to the plant. These injuries were coded as follows:
 G=General necrosis
 W=Wilting
 S=Stunting
 C=Chlorosis
 F=Formative Table V presents the activity of typical carboxamides of the present invention when evaluated in the plant disease test described above.

TABLE V

| Example No. of Compound Tested | Powdery Mildew Disease Rating | Phytotoxicity Rating | Phytotoxicity Rating |
|---|---|---|---|
| 1 | 5 | 2 | G |

TABLE V-continued

| | | | |
|---|---|---|---|
| 2 | 5 | 1 | |
| 3 | 1 | 1 | |
| 4 | 1 | 1 | |
| 5 | 5 | 1 | |
| 6 | 3 | 1 | |
| 7 | 1 | 1 | |
| 8 | 1 | 2 | G |
| 9 | 1 | 1 | |
| 10 | 3 | 1 | |
| 11 | 4 | 1 | |
| 12 | 1 | 1 | |
| 13 | 5 | 1 | |
| 14 | 4 | 1 | |
| 15 | 4 | 1 | |
| 16 | 4 | 1 | |
| 17 | 3 | 1 | |
| 18 | 5 | 2 | G |
| 19 | 1 | 1 | |
| 20 | 1 | 1 | |
| 21 | 1 | 1 | |
| 22 | 1 | 1 | |
| 23 | 4 | 1 | |
| 24 | 1 | 1 | |
| 25 | 1 | 1 | |
| 26 | 3 | 1 | |
| 27 | 3 | 1 | |
| 28 | 1 | 1 | |
| 29 | 1 | 1 | |
| 30 | 3 | 2 | S |
| 31 | 5 | 1 | |
| 32 | 5 | 2 | C |
| 33 | 1 | 1 | |
| 34 | 5 | 1 | |
| 35 | 5 | 1 | |
| 36 | 5 | 2 | C |
| 37 | 5 | 1 | |
| 38 | 4 | 1 | |
| 39 | 1 | 1 | |
| 40 | 4 | 1 | |
| 41 | 5 | 1 | |
| 42 | 5 | 1 | |
| 43 | 3 | 1 | |
| 44 | 5,5 | 2,1 | G |
| 45 | 3 | 1 | |
| 46 | 1 | 1 | |
| 47 | 3 | 2 | G |
| 49 | 4 | 1 | |
| 50 | 1 | 1 | |
| 51 | 3 | 3 | G |
| 52 | 3 | 2 | C |
| 53 | 1 | 1 | |
| 55 | 5 | 2 | C |
| 56 | 5 | 1 | |
| 58 | 1 | 1 | |
| 59 | 1 | 1 | |
| 60 | 1 | 1 | |
| 61 | 3 | 1 | |
| 62 | 3 | 1 | |
| 63 | 4 | 1 | |
| 65 | 1 | 1 | |
| 66 | 1 | 1 | |
| 67 | 1 | 1 | |
| 68 | 1 | 1 | |
| 70 | 1 | 1 | |
| 71 | 1 | 1 | |
| 72 | 1 | 1 | |
| 73 | 1 | 1 | |
| 74 | 1 | 1 | |
| 75 | 1 | 1 | |
| 76 | 1 | 1 | |
| 78 | 1 | 1 | |
| 80 | 1 | 1 | |

| Example No. of Compound Tested | Powdery Mildew Disease Rating | Phytotoxicity Rating | Phytotoxicity Type |
|---|---|---|---|
| 82 | 1 | 1 | |
| 83 | 3 | 1 | |
| 85 | 1 | 1 | |
| 87 | 1 | 1 | |
| 88 | 5 | 1 | |

Some of the compounds tested in the initial screen outlined above were evaluated further in one or both of the following two secondary screens.

Experiment 5

Compounds tested in this plant disease foliage screen were formulated in the same manner as described above for Experiment 4. The 400 ppm concentration obtained by this procedure was then serially diluted to obtain solutions having a lower concentration of test compound. The formulations were sprayed on bean plants in the same manner as described above. One day after treatment, the host plants were inoculated with powdery mildew spores. After a suitable incubation period, when disease symptoms appeared on untreated control plants, treatments were rated for disease severity according to the rating system described above. The results are recorded in Table VI.

TABLE VI

| Example No. of Compound Tested | Concentration ppm | Powdery Mildew Disease Rating | Phytotoxicity Rating | Phytotoxicity Type |
|---|---|---|---|---|
| 13 | 400 | 4 | 1 | |
| | 400 | 5 | 1 | |
| | 100 | 4 | 1 | |
| | 25 | 3 | 1 | |
| 15 | 400 | 1 | 1 | |
| 16 | 400 | 1 | 1 | |
| 18 | 400 | 1 | 1 | |
| 23 | 400 | 4 | 1 | |
| | 400 | 4 | 1 | |
| | 100 | 4 | 1 | |
| | 100 | 4 | 1 | |
| | 25 | 3 | 1 | |
| | 25 | 3 | 1 | |
| | 6 | 3 | 1 | |
| 26 | 400 | 5 | 2 | C |
| | 400 | 4 | 1 | |
| | 100 | 1 | 1 | |
| | 25 | 1 | 1 | |
| 27 | 400 | 1 | 1 | |
| 31 | 400 | 5 | 1 | |
| | 400 | 5 | 1 | |
| | 100 | 3 | 1 | |
| | 25 | 1 | 1 | |
| 35 | 400 | 4 | 1 | |
| | 400 | 4 | 1 | |
| | 100 | 3 | 1 | |
| | 25 | 1 | 1 | |
| 38 | 400 | 3 | 1 | |
| 40 | 400 | 4 | 1 | |
| | 400 | 4 | 1 | |
| | 100 | 3 | 1 | |
| | 25 | 1 | 1 | |
| 42 | 400 | 1 | 1 | |
| 44 | 400 | 5 | 1 | |
| | 400 | 5 | 1 | |
| | 100 | 5 | 1 | |
| | 100 | 5 | 1 | |
| | 25 | 5 | 1 | |
| | 25 | 4 | 1 | |
| | 6 | 5 | 1 | |
| 64 | 400 | 1 | 1 | |

Experiment 6

Compounds were again formulated as above and tested for control of wheat powdery mildew. Test compound concentrations of 400, 100 or 25 ppm were foliar sprayed onto wheat seedings in individual pots. One day later, all wheat plants were inoculated with powdery mildew spores (*Erysiphe graminis tritici*). After a suitable incubation period when disease symptoms had appeared on untreated plants, treatments were rated for disease severity. Compounds were rated as above, and the results appear in Table VII.

TABLE VII

| Example No. of Compound Tested | Concentration ppm | Wheat Powdery Mildew Disease Rating | Phytotoxicity Rating | Phytotoxicity Type |
|---|---|---|---|---|
| 1 | 400 | 1 | 1 | |
| 16 | 400 | 1 | 1 | |
|  | 400 | 1 | 1 | |
| 18 | 400 | 1 | 1 | |
| 19 | 400 | 3 | 1 | |
|  | 400 | 3 | 1 | |
|  | 400 | 1 | 1 | |
|  | 100 | 1 | 1 | |
|  | 25 | 1 | 1 | |
| 20 | 400 | 4 | 2 | G |
|  | 400 | 3 | 2 | S |
|  | 400 | 1 | 1 | |
|  | 100 | 1 | 1 | |
|  | 25 | 1 | 1 | |
| 22 | 400 | 1 | 2 | |
| 23 | 400 | 1 | 1 | |
| 24 | 400 | 1 | 1 | |
| 26 | 400 | 1 | 1 | |
| 27 | 400 | 1 | 1 | |
| 28 | 400 | 1 | 1 | |
| 29 | 400 | 1 | 1 | |
| 31 | 400 | 1 | 2 | S |
| 32 | 400 | 4 | 1 | |
|  | 400 | 3 | 1 | |
|  | 100 | 1 | 1 | |
|  | 25 | 1 | 1 | |
| 33 | 400 | 1 | 1 | |
| 34 | 400 | 1 | 1 | |
| 35 | 400 | 1 | 1 | |
| 36 | 400 | 1 | 1 | |
| 39 | 400 | 1 | 1 | |
| 40 | 400 | 1 | 1 | |
| 41 | 400 | 4 | 1 | |
|  | 400 | 3 | 1 | |
|  | 100 | 3 | 1 | |
|  | 25 | 1 | 1 | |
| 42 | 400 | 3 | 1 | |
| 44 | 400 | 5 | 2 | G |
|  | 400 | 4 | 3 | G |
|  | 400 | 4 | 1 | |
|  | 100 | 1 | 1 | |
|  | 25 | 1 | 1 | |
| 45 | 400 | 1 | 1 | |
| 46 | 400 | 1 | 1 | |
| 47 | 400 | 1 | 1 | |
| 49 | 400 | 4 | 1 | |
|  | 400 | 1 | 1 | |
|  | 100 | 1 | 1 | |
|  | 25 | 1 | 1 | |
| 50 | 400 | 1 | 1 | |
| 51 | 400 | 1 | 1 | |
| 52 | 400 | 1 | 1 | |
| 58 | 400 | 1 | 1 | |
| 61 | 400 | 1 | 1 | |
| 64 | 400 | 3 | 1 | |
| 65 | 400 | 1 | 1 | |

TABLE VII-continued

| Example No. of Compound Tested | Concentration ppm | Wheat Powdery Mildew Disease Rating | Phytotoxicity Rating | Phytotoxicity Type |
|---|---|---|---|---|
| 67 | 400 | 1 | 1 | |
| 74 | 400 | 1 | 1 | |
| 75 | 400 | 1 | 1 | |
| 76 | 400 | 1 | 2 | S |
| 78 | 400 | 1 | 1 | |
| 80 | 400 | 1 | 1 | |
| 83 | 400 | 1 | 1 | |
| 85 | 400 | 1 | 1 | |

Experiment 7

A number of compounds of the present invention were also tested to evaluate their ability to control fungal diseases that commonly infest turfgrasses.

The compound to be tested was formulated by dissolving the compound in an appropriate organic solvent such as acetone. This solution was then serially diluted with water to provide sprayable formulations for application rates of 0.5, 1, 2 and 4 pounds of active ingredient per acre. Each formulated test compound was tested against four different fungal diseases. Each compound was foliar applied to Penncross creeping bentgrass (*Agrostis palustrils*) which was then artificially inoculated with Rhizoctonia spawn (*Rhizoctonia solani*) and dollarspot spawn (*Sclerotinia homoeocarpa*) in separate pots. The formulated compound was also foliar applied to common Kentucky bluegrass (*Poa pratensis*) prior to the grass being artificially inoculated with a spore suspension of *Helminthosporium sativum*. Pennfine perennial ryegrass (*Lolium perenne*) was treated with a test compound prior to being inoculated with *Pythium aphanidermatum*. All of the individually treated, inoculated turf pots were incubated at 27° C. with greater than 90% relative humidity. The treatments were then visually evaluated 7 and 14 days following treatment for disease severity and turfgrass tolerance according to the following scales:

| Disease Severity | Turfgrass Tolerance |
|---|---|
| 5 = no disease | 1 = no injury |
| 4 = slight disease | 2 = slight injury |
| 3 = moderate disease | 3 = moderate injury |
| 2 = severe disease | 4 = severe injury |
| 1 = 100% of plant tissue is infected | 5 = death of turf |

The results of this experiment appear below in Table VIII. The numbers in parentheses refer to turfgrass tolerance ratings.

TABLE VIII

| Example No. of Compound Tested | Application Rate (lbs./acre) | 7 Days Helminthsporium | Pythium | Rhizoctonia | Schlerotinia | 14 Days Helminthsporium | Pythium | Rhizoctonia | Schlerotinia |
|---|---|---|---|---|---|---|---|---|---|
| 31 | 0.5 | 4 | 1 | 4.5 | 4.5 | 4.5 | 1 | 4 | 5 |
|  | 1.0 | 5 | 1 | 5 | 5 | 4.5 | 1 | 5 | 5 |
|  | 2.0 | 5 | 1 | 5(2) | 5(2) | 4.5 | 1 | 5 | 5 |
|  | 4.0 | 5(2) | 1 | 5(3) | 5(3) | 4.5 | 1 | 5(3) | 5(3) |
| 44 (read after 10 days) | 0.5 | 4,5 |  | 5,5 | 5,5 |  |  |  |  |
|  | 1.0 | 5,5 |  | 5,5 | 5,5 |  |  |  |  |
|  | 2.0 | 5 |  | 5(2) | 5 |  |  |  |  |
|  | 4.0 | 5 |  | 5(2) | 5 |  |  |  |  |
| 55 | 0.5 | 3.5 | 1 | 5 | 3.5 | 4.5 | 1 | 4 | 4 |
|  | 1.0 | 4.5 | 2 | 5 | 5 | 5 | 3 | 5 | 5 |
|  | 2.0 | 5 | 4 | 5(2) | 5 | 5 | 4 | 5 | 5 |
|  | 4.0 | 5(2) | 4 | 5(3) | 5(2) | 5 | 4 | 5(3) | 5(3) |

TABLE VIII-continued

| Example No. of Compound Tested | Application Rate (lbs./acre) | 7 Days Helminthsporium | Pythium | Rhizoctonia | Schlerotinia | 14 Days Helminthsporium | Pythium | Rhizoctonia | Schlerotinia |
|---|---|---|---|---|---|---|---|---|---|
| 56 | 0.5 | 2 | 1 | 4.5 | 5 | 1 | 1 | 2 | 1 |
|  | 1.0 | 3 | 1 | 4.5 | 5 | 3 | 1 | 2 | 1 |
|  | 2.0 | 5 | 1 | 5(2) | 5 | 4 | 1 | 3 | 3 |
|  | 4.0 | 5(2) | 1 | 5(3) | 5(2) | 4.5 | 1 | 3(3) | 3(3) |
| 57 | 0.5 | 3 | 1 | 5 | 4.5 | 4 | 1 | 5 | 4.5 |
|  | 1.0 | 4 | 1 | 5 | 4.5 | 4 | 1 | 5 | 4.5 |
|  | 2.0 | 5 | 3 | 5 | 4.5 | 4 | 2 | 5 | 5 |
|  | 4.0 | 5 | 3 | 5(2) | 5(2) | 4 | 3 | 5(2) | 5(2) |
| 77 | 0.5 | 1 | 1 | 1 | 1 | 1 | 1 | 1 | 1 |
|  | 1.0 | 1 | 1 | 1 | 1 | 3 | 1 | 1 | 2 |
|  | 2.0 | 1 | 1 | 1 | 1 | 3 | 3 | 2 | 2 |
|  | 4.0 | 1 | 1 | 1 | 1 | 3 | 3 | 2 | 2 |
| 84 | 0.5 | 1 | 1 | 1 | 2 | 1 | 1 | 1 | 2 |
|  | 1.0 | 1 | 1 | 1 | 2 | 1 | 1 | 1 | 2 |
|  | 2.0 | 1 | 1 | 1 | 2 | 1 | 1 | 1 | 2 |
|  | 2.0 | 1 | 1 | 1 | 2(2) | 1 | 1 | 1 | 3(3) |
| 87 | 0.5 | 1 | 1 | 3 | 1 | 1 | 1 | 4 | 1 |
|  | 1.0 | 1 | 1 | 4 | 1 | 1 | 1 | 4 | 1 |
|  | 2.0 | 1 | 1 | 4 | 1 | 1 | 1 | 4 | 1 |
|  | 4.0 | 1 | 1 | 4 | 1 | 1 | 1 | 4.5 | 1 |
| 88 | 0.5 | 5 | 1 | 5 | 5 | 5 | 1 | 5 | 5 |
|  | 1.0 | 5 | 1 | 5 | 5 | 5 | 1 | 5 | 5 |
|  | 2.0 | 5 | 1 | 5 | 5 | 5 | 1 | 5(2) | 5(2) |
|  | 4.0 | 5 | 1 | 5(2) | 5(2) | 5(2) |  |  |  |
| 89 | 0.5 | 1 | 1 | 1 | 1 | 1 | 1 | 1 | 1 |
|  | 1.0 | 1 | 1 | 1 | 1 | 1 | 1 | 1 | 1 |
|  | 2.0 | 1 | 1 | 1 | 1 | 1 | 1 | 1 | 1 |
|  | 4.0 | 1 | 1 | 2 | 1 | 1 | 1 | 1(2) | 1(2) |

Certain of the compounds provided by the present invention have also exhibited anticoccidial activity. For example, the compound of Example 63 exhibited activity against *E. tenella* at a concentration of 1 ppm as measured by a standard in vitro screening procedure. Other compounds of the present invention were also active in this screen. When used to treat coccidial infections in animals, such as poultry, the compounds are administered at doses in the range of from about 0.5 ppm to about 50 ppm, preferably from about 1 ppm to about 25 ppm.

Some of the compounds disclosed herein have also exhibited activity as aquatic algicides. For instance, the compound of Example 66 has exhibited 100% control against *Scenedesmus quadricauda* at an application rate of 0.5 ppm. as measured by a standard aquatic algicide screen. The compound of Example 70 has exhibited 100% control against *Anacystis nidulans* at 10 ppm. Other compounds of the invention have exhibited activity against the aquatic algae species *Chlorella vulgaris* and *Stichococcus bascillaris* in the same screen. When employed as algicides, the compounds may be applied at rates of from about 0.1 ppm to about 20 ppm, preferably 0.5 ppm to about 10 ppm.

The present compounds have also been found to display excellent terrestrial plant growth regulation activity, for example in controlling the growth of shoots and roots in plants such as beans, peas, wheat and the like. The compounds are especially useful in controlling the growth of turfgrasses, and as such can be employed as chemical lawn mowers. The compounds are generally applied at rates effective to regulate plant growth without causing substantial plant toxicity. Such plant growth regulation rates will be in the range of from about 1 to 2000 ppm, preferably 25 to 1000 ppm.

A further embodiment of the present invention are agricultural formulations comprising an N,N-disubstituted carboxamide derivative of the invention together with a suitable carrier, excipient, or diluent therefor. The compounds may be formulated in a variety of ways depending on the desired utility.

When the compounds of the present invention are to be used as coccidiostats, they may be formulated as a feed pre-mix with a suitable physiologically-acceptable carrier or diluent. Suitable carriers include rice hulls, ground corn cobs, and the like. Typically the compounds are administered by mixing the formulated pre-mix in the animal's feed.

For use as herbicides, fungicides, algicides and similar agricultural uses, the compounds of the present invention will be formulated with a suitable agriculturally-acceptable carrier or diluent. Such compositions will contain from about 0.1 to about 95.0 percent by weight of the active ingredient, depending on the composition desired. Preferred formulations will contain from about 1 to about 50 percent active ingredient. Sprayable formulations are preferred, because of the rapidity and economy of application, and because the sprayed applications do not drift to untreated areas as would some formulations, for example, a dust.

Dust compositions are contemplated and will contain a compound of the present invention generally in an amount from about 0.1 to about 5 percent by weight. Dusts are prepared by intimately mixing and finely grinding the compound with an inert solid diluent or carrier such as ground montmorillonite clay, attapulgite clay, talc, ground volcanic rock, kaolin clay, or other inert, relatively dense, inexpensive substances.

The most convenient formulations contemplated are in the form of concentrated compositions. Such formulations are diluted with water, generally at or near the site of application and are applied by spraying the resulting water dispersion or emulsion. The diluted compositions generally will contain the active compounds in the range from about 0.1 percent to about 10 percent by weight. Water-dispersible or emulsifiable compositions may be either solids, usually known as wettable powders, or liquids, usually known as emulsifiable concentrates or aqueous suspensions.

A typical wettable powder comprises an intimate mixture of a compound of the invention, an inert carrier, and one or more surfactants. The concentration of the active compound is usually from about 5 percent to about 90 percent by weight, ideally about 10 to about 70 percent. The inert carrier is usually chosen from among the attapulgite clays, the montmorillonite clays, the diatomaceous earths, the purified silicates, or other similar substances that are readily available. Effective surfactants, comprising from about 0.5 percent to about 10 percent by weight of the wettable powder, are chosen from among the sulfonated lignins, the condensed naphthalenesulfonates, the alkyl sulfates, and related materials.

A typical emulsifiable concentrate comprises from about 0.1 to about 6 pounds of a compound of the invention per gallon of liquid, dissolved in a mixture of an organic solvent and an emulsifier. The organic solvent is chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as alkylphenol adducts of polyoxyethylene, and are used at similar percentages as for wettable powders.

Solid, granular compositions are convenient for the application of compounds of this invention to the soil. Granules comprise a compound of the invention dispersed on a granular inert carrier such as coarsely ground clay of from about 0.1 to about 3 mm. particle size. The compound is most conveniently applied to the clay by dissolving it in an inexpensive solvent such as acetone and applying the solution to the sized clay in an appropriate solids mixer. The solvent is then removed by evaporation or the like.

The formulated compounds are applied to plants and to the locus where plants are growing in the manners conventional in agricultural chemistry. Sprayable compositions are easily applied by any of many types of sprayers available to the art. Self-propelled, tractor-mounted, and towed spray devices which apply the water-dispersed formulations through calibrated atomizing nozzles are available and effective. Metering applicators are also available which can apply accurately measured quantities of granular compositions to the locus to be treated. The operator of the application equipment need only take care to adjust the equipment to apply an amount of the water-dispersed or granular formulation which supplies the desired application rate of the compound, and to apply the amount uniformly to the plants to be treated.

The following examples provide an illustration of typical agricultural compositions comprehended by this invention.

EXAMPLE 90

Wettable Powder

| Ingredient | Concentration by weight (%) |
| --- | --- |
| N—(2,4-dichlorophenyl-N—[(3-pyridyl)- | 50 |
| methyl]-2,2-dimethylpropanamide | |
| Igepal CA = 6.30, a polyoxyethylene octyl phenol nonionic wetting agent-GAF Corp. | 20 |
| Bardens Clay | 30 |

The N,N-disubstituted carboxamide is finely divided into a powder and blended to uniformity with the agronomic carriers to form a free flowing powder that will be wetted and suspendible in water at or near the site of application to form a sprayable mixture. The composition is then sprayed on the locus where control is desired. The application is done at a volume rate so that the active ingredient is present at about 1 to about 4 pounds per acre (about 1.12 to about 4.48 kg./ha.).

EXAMPLE 91

Dust

| Ingredient | Weight (%) |
| --- | --- |
| N—(2,6-dimethylphenyl)-N—[(3-pyridyl)methyl]-(2-chloroethylamino)carboxamide | 5 |
| Diatomite, a diatomaceous earth, Witco Chemical Corp., Inorganic Specialities Division | 95 |

The carboxamide is suspended in acetone and sprayed onto the diatomaceous earth carrier. The solvent is then removed by evaporation and the dry mixture is ground to a fine powder of uniform particle size of about 10 to about 40 microns. The dust formulation can be diluted at the site of application if desired by the addition of additional excipient such as silica or clay. The dust is surface applied to the soil or plants where control is desired, either by conventional ground equipment or alreally.

EXAMPLE 92

Aqueous Suspension

| Ingredient | Weight (%) |
| --- | --- |
| N—[1-(3-pyridyl)ethyl]-N—cyclohexyl-α-(n-butylthio)acetamide | 60.0 |
| Reax, lignosulfonate suspending agent, Westvaco Corp., Polychemical Dept. | 5.0 |
| Zanthum Gum thickening agent | 0.15 |
| Zeosyl 100, a precipitated hydrated silicon dioxide anticaking agent | 1.0 |
| Antifoam C foam suppressant | 0.25 |
| Water | 33.60 |
| | 100.00 |

The aqueous supension containing the carboxamide derivative is typically diluted with additional water at the site of application, and sprayed onto the locus where vegetative control is desired. The diluted aqueous suspension is applied such that the active ingredient is present at about 4 pounds per acre for the effective control of unwanted vegetation such as lambsquarter, pigweed, velvetleaf and the like in crops such as corn, soybean, cereal grains, or in fallow land.

I claim:

1. A compound of the formula

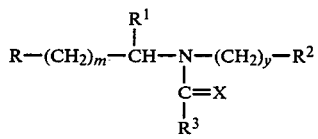

wherein:

R and $R^2$ independently are 3-pyridyl, 4-pyridyl, $C_4$–$C_{10}$ alkyl, $C_2$–$C_{10}$ alkenyl, $C_3$–$C_8$ cycloalkyl, $C_1$–$C_4$ alkyl substituted $C_3$–$C_8$ cycloalkyl, 3,4-(methylenedioxy)phenyl or phenyl substituted with one or two $C_1$–$C_6$ alkyl, $C_1$–$C_6$ alkoxy, halogen, $C_1$–$C_6$ haloalkyl, $C_1$–$C_6$ haloalkoxy or nitro groups; provided that one and only one of R and $R^2$ is 3-pyridyl or 4-pyridyl;

m and y independently are 0 or 1;

$R^1$ is H or $C_1$–$C_4$ alkyl;

x is O or S;

$R^3$ is $C_4$–$C_{10}$ branched alkyl, $C_5$–$C_8$ cycloalkyl, -$C_1$–$C_4$ alkylene-Z-$R^4$, wherein Z is O, S, or a direct link;

$R^4$ is $C_1$–$C_{10}$ alkyl, or $C_3$–$C_8$ cycloalkyl;

and the agronomically-acceptable salts thereof; with the proviso that when $R^4$ is $C_1$–$C_{10}$ alkyl, Z is not a direct link.

2. A compound of claim 1 wherein R is 3-pyridyl.

3. A compound of claim 2 wherein m and y are both 0.

4. A compound of claim 3 where in X is O.

5. A compound of claim 4 wherein $R^2$ is phenyl substituted with one or two $C_1$–$C_6$ alkyl, $C_1$–$C_6$ alkoxy, halogen, $C_1$–$C_6$ haloalkyl, $C_1$–$C_6$ haloalkoxy or nitro groups.

6. A compound of claim 5 wherein $R^3$ is $C_4$–$C_{10}$ branched alkyl.

7. A compound of claim 6 wherein $R^1$ is hydrogen.

8. The compound of claim 7 which is N-(4-chlorophenyl)-N-[(3-pyridyl)methyl]-2,2-dimethylpropanamide.

9. The compound of claim 7 which is N-(2,4-dichlorophenyl)-N-[(3-pyridyl)methyl]-2,2-dimethylpropanamide.

10. The compound of claim 7 which is N-(2-chlorophenyl)-N-[(3-pyridyl)methyl]-2,2-dimethylpropanamide.

11. The compound of claim 7 which is N-(2-methyl-4-chlorophenyl)-N-[(3-pyridyl)methyl]-2,2-dimethylpropanamide.

12. The compound of claim 7 which is N-(2,4-dichlorophenyl)-N-[(3-pyridyl)methyl]-2-methylpropanamide.

13. The compound of claim 7 which is N-(2,6-dimethylphenyl)-N-[(3-pyridyl)methyl]-2,2-dimethylpropanamide.

14. A compound of claim 6 wherein $R^1$ is methyl.

15. The compound of claim 14 which is N-(4-chlorophenyl)-N-[1-(3-pyridyl)ethyl]-2,2-dimethylpropanamide.

16. A compound of claim 5 wherein $R^3$ is -$C_1$–$C_4$ alkylene-Z-$R^4$.

17. A compound of claim 16 wherein $R^4$ is $C_1$–$C_{10}$ alkyl.

18. A compound of claim 17 wherein Z is oxygen.

19. The compound of claim 18 which is N-(4-chlorophenyl)-N-[(3-pyridyl)methyl]-2-methoxyacetamide.

20. A compound of claim 16 wherein Z is sulfur.

21. A compound of claim 1 wherein X is sulfur.

22. A compound of claim 1 which is an agronomically-acceptable salt.

23. A method for controlling the growth of fungal diseases which comprises applying to the plant for which control is desired a disease inhibiting and nonherbicidal amount of a compound of claim 1.

24. A method of claim 23 employing a compound wherein X is oxygen.

25. A method of claim 23 employing a compound wherein $R^3$ is $C_4$–$C_{10}$ branched alkyl.

26. A method of claim 23 wherein the fungal disease is powdery mildew.

27. A fungicidal composition for controlling the growth of fungal diseases of plants comprising a fungicidally-effective amount of a compound of claim 1 together with a suitable carrier, excipient, or diluent therefor.

28. A composition of claim 27 employing a compound wherein X is oxygen.

29. A composition of claim 27 employing a compound wherein $R^3$ is $C_4$–$C_{10}$ branched alkyl.

* * * * *